(12) United States Patent
Gu et al.

(10) Patent No.: US 9,322,024 B2
(45) Date of Patent: Apr. 26, 2016

(54) APTAMERS SCREENING METHOD BASED ON GRAPHENE WITHOUT TARGET IMMOBILIZATION AND THE APTAMERS OBTAINED FROM THE METHOD

(75) Inventors: Man Bock Gu, Seoul (KR); Jee Woong Park, Seoul (KR); Tatavarty Rameshwar, Houston, TX (US)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 0 days.

(21) Appl. No.: 14/342,241

(22) PCT Filed: Aug. 30, 2012

(86) PCT No.: PCT/KR2012/006927
§ 371 (c)(1),
(2), (4) Date: Feb. 28, 2014

(87) PCT Pub. No.: WO2013/032242
PCT Pub. Date: Mar. 7, 2013

(65) Prior Publication Data
US 2014/0363808 A1 Dec. 11, 2014

(30) Foreign Application Priority Data

Aug. 31, 2011 (KR) .................. 10-2011-0088066
Apr. 25, 2012 (KR) .................. 10-2012-0043230

(51) Int. Cl.
| | | |
|---|---|---|
| C07H 21/04 | (2006.01) | |
| C12N 15/115 | (2010.01) | |
| C12N 15/10 | (2006.01) | |
| C12Q 1/68 | (2006.01) | |
| G01N 33/569 | (2006.01) | |
| G01N 33/574 | (2006.01) | |
| G01N 33/68 | (2006.01) | |

(52) U.S. Cl.
CPC .......... *C12N 15/115* (2013.01); *C12N 15/1048* (2013.01); *C12Q 1/6811* (2013.01); *G01N 33/56983* (2013.01); *G01N 33/57407* (2013.01); *G01N 33/6893* (2013.01); *C12N 2310/16* (2013.01); *C12N 2320/13* (2013.01); *C12N 2330/30* (2013.01)

(58) Field of Classification Search
None
See application file for complete search history.

(56) References Cited

U.S. PATENT DOCUMENTS

| 5,660,985 A | 8/1997 | Pieken et al. |
| 2003/0143573 A1 | 7/2003 | Huchzermeier et al. |

OTHER PUBLICATIONS

Park et al. (Chem. Commun. 2012: 2071-2073).*
Cotten et al. "2'-O-methyl, 2'-O-ethyl Oligoribonucleotides and Phosphorothioate Oligodeoxyribonucleotides as Inhibitors of the in vitro U7 snRNP-Dependent mRNA Processing Event." *Nucleic Acids Res.* 19.10(1991):2629-2635.
He et al. "A Graphene Nanoprobe for Rapid, Sensitive, and Multicolor Fluorescent DNA Analysis." *Adv. Fund. Mater.* 20(2010):453-459.
Hobbs et al. "Polynucleotides Containing 2'-AMino-2'-deoxyribose and 2'-Azido-2'-deoxyribose." *Biochem.* 12.25(1973):5138-5145.
Huang et al. "Synergistic pH Effect of Reversible Shuttling Aptamer-Based Biosensors Between Graphene Oxide and Target Molecules." *J. Mater. Chem.* 21(2011):8991-8993.
Park et al. "Selection and Characterization of ssDNA Aptamers for the Nampt." *Korean Soc. Biotechnol. Bioeng.* 26(2010):213. (Abstract Only).
Pu et al "Insulin-Binding Aptamer-Conjugated Graphene Oxide for Insulin Detection." *Analyst.* 136(2011):4138-4140.
Sefah et al. "Nucleic Acid Aptamers for Biosensors and Bio-Analytical Applications." *Analyst.* 134(2009):1765-1775.
Sproat et al. "New Synthetic Routes to Synthons Suitable for 2'-O-allyloligoribonucleotide Assembly." *Nucleic Acids Res.* 19.4(1991):733-738.
Stoltenburg et al. "FluMag—SELEX as an Advantageous Method for DNA Aptamer Selection." *Anal. Bioanal. Chem.* 383(2005):83-91.

\* cited by examiner

*Primary Examiner* — Kimberly Chong
(74) *Attorney, Agent, or Firm* — Mintz Levin Cohn Ferris Glovsky and Popeo, P.C.; Fred C. Hernandez; Linyu L. Mitra

(57) ABSTRACT

Provided is aptamers screening method based on graphene without target immobilization and the aptamers obtained from the method, and more particularly, a new GO-SELEX method without target immobilization in which a single-stranded nucleic acid pool may react with a non-bound target material or a counter-target material, after which a single-stranded nucleic acid which has not been bound to the target or counter-target may be separated by using the graphene. Also, the specific aptamer obtained through the above-described method may be used for diagnosing target related diseases.

15 Claims, 31 Drawing Sheets dG=-12.85 G12 dG=-12.76 G4 dG=-12.64 G27 dG=-12.59 G35 dG=-11.83 G26 dG=-11.58 G9 dG=-10.81 G32 dG=-10.72 G21 dG=-10.55 G15 dG=-10.1254 dG=-10.07 G37 dG=-9.75 GB8 dG=-10.24 GB17 dG=-10.60 GB34 dG=-10.67 GB38

FIG. 31

[Bar chart showing Relative Binding Ratio (%) vs B1-11, B1-34, B1-43 with legend: BVDV t1, BVDV t2, CSFV, MDBK, BSA]

FIG. 32

[Graph showing Response Unit vs BVDV 1 concentration (TCID$_{50}$/mL) with three curves:
- B1-34 (Kd=4.22×10$^4$)
- B1-11 (Kd=4.08×10$^4$)
- B1-43 (Kd=5.20×10$^4$)]

FIG. 33

1st aptamer seq.
2nd aptamer seq.

FIG. 34

```
                              SEQUENCE LISTING

<160> NUMBER OF SEQ ID NOS: 28

<210> SEQ ID NO 1
<211> LENGTH: 18
<212> TYPE: DNA
<213> ORGANISM: Artificial sequence
<220> FEATURE:
<223> OTHER INFORMATION: Primer for PCR amplification

<400> SEQUENCE: 1
cgtacggaat tcgctagc                                                    18

<210> SEQ ID NO 2
<211> LENGTH: 18
<212> TYPE: DNA
<213> ORGANISM: Artificial sequence
<220> FEATURE:
<223> OTHER INFORMATION: Primer for PCR amplification

<400> SEQUENCE: 2
ggatccgagc tccacgtg                                                    18

<210> SEQ ID NO 3
<211> LENGTH: 18
<212> TYPE: DNA
<213> ORGANISM: Artificial sequence
<220> FEATURE:
<223> OTHER INFORMATION: Reward primer for PCR amplification of Nampt
      binding DNA

<400> SEQUENCE: 3
cacgtggagc tcggatcc                                                    18

<210> SEQ ID NO 4
<211> LENGTH: 65
<212> TYPE: DNA
<213> ORGANISM: Artificial sequence
<220> FEATURE:
<223> OTHER INFORMATION: Nampt specific aptamer G56

<400> SEQUENCE: 4
cgtacggaat tcgctagccc gtggggtagc ggggtcgtgt gatatgtgga tccgagctcc      60
acgtg                                                                  65

<210> SEQ ID NO 5
<211> LENGTH: 66
<212> TYPE: DNA
```

```
<213> ORGANISM: Artificial sequence
<220> FEATURE:
<223> OTHER INFORMATION: Nampt specific aptamer no. G12

<400> SEQUENCE: 5
cgtacggaat tcgctagcgg gtgccgtggc acgaggccgt ggtccagggg atccgagctc    60
cacgtg                                                               66

<210> SEQ ID NO 6
<211> LENGTH: 66
<212> TYPE: DNA
<213> ORGANISM: Artificial sequence
<220> FEATURE:
<223> OTHER INFORMATION: Nampt specific aptamer no. G4

<400> SEQUENCE: 6
cgtacggaat tcgctagcgt gatgtggggg tacgctcgtg gcaggcttgg atccgagctc    60
cacgtg                                                               66

<210> SEQ ID NO 7
<211> LENGTH: 66
<212> TYPE: DNA
<213> ORGANISM: Artificial sequence
<220> FEATURE:
<223> OTHER INFORMATION: Nampt specific aptamer no. G27

<400> SEQUENCE: 7
cgtacggaat tcgctagcgg gtggagtacg tgggggtcat cctgtgtggg atccgagctc    60
cacgtg                                                               66

<210> SEQ ID NO 8
<211> LENGTH: 66
<212> TYPE: DNA
<213> ORGANISM: Artificial sequence
<220> FEATURE:
<223> OTHER INFORMATION: Nampt specific aptamer no. G35

<400> SEQUENCE: 8
cgtacggaat tcgctagcgg tgacggacgt ggggtgcacg aagggagggg atccgagctc    60
cacgtg                                                               66

<210> SEQ ID NO 9
<211> LENGTH: 66
<212> TYPE: DNA
<213> ORGANISM: Artificial sequence
<220> FEATURE:
<223> OTHER INFORMATION: Nampt specific aptamer no. G26

<400> SEQUENCE: 9
cgtacggaat tcgctagcat cgggtgcaga gtcggagcta acggcagcgg atccgagctc    60
cacgtg                                                               66

<210> SEQ ID NO 10
<211> LENGTH: 66
<212> TYPE: DNA
<213> ORGANISM: Artificial sequence
<220> FEATURE:
<223> OTHER INFORMATION: Nampt specific aptamer no. G9

<400> SEQUENCE: 10
cgtacggaat tcgctagcgg ggatgggccg ctctgcagaa tgttctgtgg atccgagctc    60
cacgtg                                                               66
```

<210> SEQ ID NO 11
<211> LENGTH: 66
<212> TYPE: DNA
<213> ORGANISM: Artificial sequence
<220> FEATURE:
<223> OTHER INFORMATION: Nampt specific aptamer no. G32

<400> SEQUENCE: 11
cgtacggaat tcgctagcgt ggactggcgg aaatcttggt atgcccatgg atccgagctc    60
cacgtg    66

<210> SEQ ID NO 12
<211> LENGTH: 66
<212> TYPE: DNA
<213> ORGANISM: Artificial sequence
<220> FEATURE:
<223> OTHER INFORMATION: Nampt specific aptamer no. G21

<400> SEQUENCE: 12
cgtacggaat tcgctagcgg gttcgggacg gatgaacgtg atagctgagg atccgagctc    60
cacgtg    66

<210> SEQ ID NO 13
<211> LENGTH: 65
<212> TYPE: DNA
<213> ORGANISM: Artificial sequence
<220> FEATURE:
<223> OTHER INFORMATION: Nampt specific aptamer no. G15

<400> SEQUENCE: 13
cgtacggaat tcgctagcag ccggcgggtg ctcaatgttg ggggttggga tccgagctcc    60
acgtg    65

<210> SEQ ID NO 14
<211> LENGTH: 66
<212> TYPE: DNA
<213> ORGANISM: Artificial sequence
<220> FEATURE:
<223> OTHER INFORMATION: Nampt specific aptamer no. G40

<400> SEQUENCE: 14
cgtacggaat tcgctagccg gggtgggaac cagtcttgcg cgggtgacgg atccgagctc    60
cacgtg    66

<210> SEQ ID NO 15
<211> LENGTH: 66
<212> TYPE: DNA
<213> ORGANISM: Artificial sequence
<220> FEATURE:
<223> OTHER INFORMATION: Nampt specific aptamer no. G54

<400> SEQUENCE: 15
cgtacggaat tcgctagcgt ggcggggcgc gggtgccgga gttgatgtgg atccgagctc    60
cacgtg    66

<210> SEQ ID NO 16
<211> LENGTH: 66
<212> TYPE: DNA
<213> ORGANISM: Artificial sequence
<220> FEATURE:
<223> OTHER INFORMATION: Nampt specific aptamer no. G37

```
<400> SEQUENCE: 16
cgtacggaat tcgctagcgg gcgatgtgcg gaatgtggga ttgcgggtgg atccgagctc     60
cacgtg                                                                66

<210> SEQ ID NO 17
<211> LENGTH: 66
<212> TYPE: DNA
<213> ORGANISM: Artificial sequence
<220> FEATURE:
<223> OTHER INFORMATION: Nampt specific aptamer no. G39

<400> SEQUENCE: 17
cgtacggaat tcgctagcgg ttgccgtgcg gcgtgcgagt tgggccttgg atccgagctc     60
cacgtg                                                                66

<210> SEQ ID NO 18
<211> LENGTH: 66
<212> TYPE: DNA
<213> ORGANISM: Artificial sequence
<220> FEATURE:
<223> OTHER INFORMATION: Nampt specific aptamer no. G55

<400> SEQUENCE: 18
cgtacggaat tcgctagcgg actggagtct agaccgggta gctgtggtgg atccgagctc     60
cacgtg                                                                66

<210> SEQ ID NO 19
<211> LENGTH: 66
<212> TYPE: DNA
<213> ORGANISM: Artificial sequence
<220> FEATURE:
<223> OTHER INFORMATION: BVDV type 1 specific aptamer no. B1-13

<400> SEQUENCE: 19
cgtacggaat tcgctagctt gggtataacg ttctgagtca gaacgccggg atccgagctc     60
cacgtg                                                                66

<210> SEQ ID NO 20
<211> LENGTH: 66
<212> TYPE: DNA
<213> ORGANISM: Artificial sequence
<220> FEATURE:
<223> OTHER INFORMATION: BVDV type 1 specific aptamer no. B1-38

<400> SEQUENCE: 20
cgtacggaat tcgctagcac ggcgggtcgc ccgactttgg gccgactggg atccgagctc     60
cacgtg                                                                66

<210> SEQ ID NO 21
<211> LENGTH: 66
<212> TYPE: DNA
<213> ORGANISM: Artificial sequence
<220> FEATURE:
<223> OTHER INFORMATION: BVDV type 1 specific aptamer no. B1-34

<400> SEQUENCE: 21
cgtacggaat tcgctagccg ctcggggcgc tgcacgtagg gtggggtggg atccgagctc     60
cacgtg                                                                66

<210> SEQ ID NO 22
<211> LENGTH: 66
```

```
<212> TYPE: DNA
<213> ORGANISM: Artificial sequence
<220> FEATURE:
<223> OTHER INFORMATION: BVDV type 1 specific aptamer no. B1-17

<400> SEQUENCE: 22
cgtacggaat tcgctagcgt ggggcagttg cttgatgatc tgtagcgcgg atccgagctc    60
cacgtg                                                                66

<210> SEQ ID NO 23
<211> LENGTH: 66
<212> TYPE: DNA
<213> ORGANISM: Artificial sequence
<220> FEATURE:
<223> OTHER INFORMATION: BVDV type 1 specific aptamer no. B1-11

<400> SEQUENCE: 23
cgtacggaat tcgctagctg cgcatccaca aatgtattgt cggggatgg atccgagctc     60 cacgtg                                                                66

<210> SEQ ID NO 24
<211> LENGTH: 66
<212> TYPE: DNA
<213> ORGANISM: Artificial sequence
<220> FEATURE:
<223> OTHER INFORMATION: BVDV type 1 specific aptamer no. B1-39

<400> SEQUENCE: 24
cgtacggaat tcgctagccg ggtctagtca ggaggttcct gtggtgctgg atccgagctc    60
cacgtg                                                                66

<210> SEQ ID NO 25
<211> LENGTH: 66
<212> TYPE: DNA
<213> ORGANISM: Artificial sequence
<220> FEATURE:
<223> OTHER INFORMATION: BVDV type 1 specific aptamer no. B1-8

<400> SEQUENCE: 25
cgtacggaat tcgctagcga gggcgccaaa cagggtgtcc tggcgttggg atccgagctc    60
cacgtg                                                                66

<210> SEQ ID NO 26
<211> LENGTH: 66
<212> TYPE: DNA
<213> ORGANISM: Artificial sequence
<220> FEATURE:
<223> OTHER INFORMATION: BVDV type 1 specific aptamer no. B1-43

<400> SEQUENCE: 26
cgtacggaat tcgctagctg cggactcgcg atgctacttc tgatgatagg atccgagctc    60
cacgtg                                                                66

<210> SEQ ID NO 27
<211> LENGTH: 66
<212> TYPE: DNA
<213> ORGANISM: Artificial sequence
<220> FEATURE:
<223> OTHER INFORMATION: BVDV type 1 specific aptamer no. B1-27

<400> SEQUENCE: 27
cgtacggaat tcgctagcta agggtagcac aggtcacctc gccactgtgg atccgagctc    60
```

```
cacgtg                                                              66

<210> SEQ ID NO 28
<211> LENGTH: 66
<212> TYPE: DNA
<213> ORGANISM: Artificial sequence
<220> FEATURE:
<223> OTHER INFORMATION: BVDV type 1 specific aptamer no. B1-40

<400> SEQUENCE: 28
cgtacggaat tcgctagccg aacgttgcgg tgtggaactt cgcgagcagg atccgagctc    60
cacgtg                                                              66
```

APTAMERS SCREENING METHOD BASED ON GRAPHENE WITHOUT TARGET IMMOBILIZATION AND THE APTAMERS OBTAINED FROM THE METHOD

CROSS-REFERENCE TO RELATED APPLICATION

This application is a national stage application, filed under 35 U.S.C. §371, of International Application No. PCT/KR2012/006927, filed Aug. 30, 2012, which claims priority to and the benefit of Korean Patent Application No. 2011-0088066, filed Aug. 31, 2011 and 2012-0043230, filed Apr. 25, 2012, the contents of which are incorporated herein by reference in their entireties.

INCORPORATION-BY-REFERENCE OF SEQUENCE LISTING

The contents of the text file named "46278-511N01US_ST25.txt", which was created on Feb. 28, 2014 and is 8 KB in size, are hereby incorporated by reference in their entireties.

BACKGROUND

1. Field of the Invention

The present invention relates to aptamers screening method based on graphene without target immobilization in which a single-stranded nucleic acid pool reacts with a non immobilized target material and a single-stranded nucleic acid which has not been bound to the target material or a counter-target material is separated using the graphene, and also relates to specific aptamers selected by the method.

2. Discussion of Related Art

In the conventional biosensor field, an antibody is superior in terms of sensitivity to other various sensing materials used to detect a target material. However, antibodies have a problem in that a process of injecting a target material (antigen) to be detected into an animal's body, obtaining an antibody produced by the animal's biological immune system, and performing a purification process is time-consuming and costly. Further, as compared with aptamers that are rarely limited in target materials, there is a limit in target materials that can be used as antigens. Therefore, it is difficult to manufacture antibodies to low molecular chemical substances such as toxic substances. Typically, an antibody is a very big protein having a size of 100 KDa or more, and thus, when it is used for an electrochemistry-based biosensor, it may be limited in signal detection, and it is remarkably inferior in terms of thermostability to DNA or other chemical substances. Therefore, a conventional technique using an antibody for diagnosing a blood biomarker is not efficient in terms of cost and time, cannot be applied to various fields and is limited in application as a biosensor.

As a novel sensing material to solve such problems, an aptamer which is a nucleic acid construct having a specifically high affinity to various target materials has been used in many studies.

An aptamer is a single-stranded DNA or RNA construct having high specificity and affinity to a specific target. Since an aptamer has a high affinity to a target, has an excellent thermostability and can be synthesized in vitro, it is superior in terms of cost to other sensing materials used in the conventional sensor field. Further, there is no limit in a target material, and thus it is possible to synthesize aptamers with respect to various targets including biomolecules such as proteins, amino acids, etc., small organic chemical substances such as endocrine disruptors or antibiotics, and bacteria. In recent years, due to characteristics of aptamers specifically bound to target materials, many studies on developing an aptamer for application to new drug development, a drug delivery system, and biosensors have been conducted.

The most important factor in a method for developing an aptamer is to distinguish DNA (or RNA) which is bound to a target from DNA which is not bound to the target. To do so, studies on distinguishing DNA by typically immobilizing a target or immobilizing a DNA random library have been conducted. However, the biggest problem of such an immobilization method is that immobilized yield can be low and it is costly and time-consuming to analyze the immobilized yield. Further, the possibility of DNA being directly bound to a separation material (magnetic beads, columns, etc.) used for immobilization cannot be entirely excluded, and the possibility of loss of a DNA pool which may occur when the DNA bound to a target immobilized to the separation material is separated again remains as a limit and problem of the immobilization method. In particular, a low DNA immobilization rate problem which may occur when a DNA library is immobilized is directly related to loss of a DNA pool which is the biggest loss to be avoided during an aptamer development process and thus serves as an upper limit. Moreover, it is difficult to develop aptamers by the immobilization method for heavy metal ions which cannot be immobilized, and thus the immobilization method may be limited in target selection. However, the above-described limits can be overcome by immobilization-free developing technology of aptamer. Further, since a binding site of a target is not limited, it is possible to reduce the number of repetitions of a selection process required for development of an aptamer. Therefore, in order to invent a technique by which an aptamer can be developed through a immobilization-free method, a microelectromechanical system (MEMS), capillary electrophoresis, etc. have been conventionally used, but expensive equipment, complexity in use of devices, necessity of skilled manpower, and the like still remain as problems. Meanwhile, graphene is a two-dimensional carbon structure having excellent thermostability, electrical characteristics, and strength and is bound to a base of a single-stranded DNA by π-stacking, and thus a wide range of studies using such characteristics have been conducted.

Adipokines are proteins secreted from adipocytes and tissues and plays an important role in metabolism. One of adipokine, Nampt (Nicotinamide phosphoribosyltransferase) is a visceral fat-derived protein that has been newly found in recent years and is reported as being closely related to type-2 diabetes caused by obesity. Further, Nampt induces angiogenesis of cancer cells and thus it is an important biomarker associated with colorectal cancer, prostate cancer, stomach cancer, breast cancer, etc. and is also associated with various diseases such as polycystic ovarian syndrome, chronic renal failure, chronic obstructive lung disease, etc.

Meanwhile, bovine viral diarrhea is a disease that causes ulcers in gastrointestinal mucous membranes, diarrhea, respiratory diseases, and death in severe cases. A Bovine Viral Diarrhea Virus type 1 causing bovine viral diarrhea is one of the main threats to the livestock industry. If a pregnant cow is infected, fetal infection occurs highly frequently and various disabilities such as still birth and congenital anomalies occur. A fetus born after being infected at an early gestational stage may carry the virus throughout its life and serve as a source of new infections. In a route of infection with bovine viral diarrhea, infection from a persistently infected cow is considered significant. Therefore, in order to effectively conduct disease surveillance and quarantine activities against bovine viral diarrhea, it is necessary to separate or detect the virus from bovine serum and tissues by a rapid and accurate test method. In this regard, there is reported a method of detecting whether a tissue of a target animal tests positive or negative for the Bovine Viral Diarrhea Virus using an antibody specific to the Bovine Viral Diarrhea Virus epitope (US 2003/0143573). However, conventionally, a method using an antibody for diagnosis has been reported as time-consuming and costly since it is necessary to inject a target material (antigen) to be detected into an animal's body to obtain an antibody produced by the animal's biological immune system, and it is also necessary to perform a purification process. Further, there is a limit in target materials that can be used as antigens. Therefore, it is difficult to manufacture antibodies to toxic substances or viruses. Furthermore, an antibody is a very big protein having a size of 100 KDa or more, and thus, when it is used as an electrochemistry-based biosensor, it may be limited in signal detection, and it is remarkably inferior in terms of thermostability to DNA or other chemical substances, and thus may be limited in application to diagnosis. However, conventionally, there has not been reported an aptamer targeting the Bovine Viral Diarrhea Virus.

The present inventors completed the present invention based on the findings that when graphene is used in developing an aptamer, it is possible to develop an aptamer without a process of immobilizing a target, thereby solving all the problems of the conventional techniques such as limits in binding sites of a target, which may occur when the target is immobilized, and also possible to develop a DNA aptamer without skilled manpower or expensive equipment, and a nucleic acid aptamer capable of firstly diagnosing relevant diseases more accurately and rapidly by accurately measuring a concentration of Nampt, which is a target model, as an important biomarker for type 2 diabetes and cancers, and secondly being specifically bound to a Bovine Viral Diarrhea Virus type 1 only without being bound to other similar substances (BVDV type 2, MDBK cell, Bovine Serum albumin, etc.) for diagnosing bovine viral diarrhea more accurately and rapidly has been developed.

SUMMARY OF THE INVENTION

One object of the present invention is to provide a method for developing a graphene nanomaterial-based aptamer without using a separate device by means of an immobilization-free method.

Another object of the present invention is to provide a nucleic acid aptamer nanostructure as a sensing material with high sensitivity which can be specifically bound to a target such as a specific protein in a small amount, a low molecular substance, and a virus but is not bound to other biomaterials in a blood sample, using the method for developing a graphene-based aptamer.

Still another object of the present invention is to detect or separate a specific protein, virus, or the like using the specific aptamer and also diagnose diseases related to the specific protein, virus, or the like.

In order to achieve the above-described objects, one aspect of the present invention provides a method for producing a nucleic acid aptamer without target immobilization comprising: reacting a single-stranded nucleic acid pool including a PCR primer region at both ends and any 30 to 50 bases at its center with a target material or a counter-target material and adding graphene; and separating a target specific nucleic acid aptamer by removing a target non-specific single-stranded nucleic acid bound to the graphene, or separating a target specific nucleic acid aptamer from the graphene by causing a conformational change by the target material on a target specific single-stranded nucleic acid bound to the graphene.

To be more specific, the method for producing a nucleic acid aptamer without target immobilization comprises the following steps:

a first step in which a single-stranded nucleic acid pool including a PCR primer region at both ends and any 30 to 50 bases at its center is mixed with a target material or a counter-target material in a buffer solution and these are induced to be bound to each other at normal temperature;

a second step in which the mixture solution is reacted with graphene to remove a single-stranded nucleic acid which is not bound to the target material or the counter-target material;

a third step in which a single-stranded nucleic acid specifically bound to the target material and obtained in the above step is amplified by performing a PCR using the PCR primer region;

a fourth step in which a graphene-based selection process and a counter selection process are repeatedly carried out on the single-stranded nucleic acid specifically bound to the target material using the target material and the counter-target material; and a fifth step in which a target non-specific single-stranded nucleic acid bound to the counter-target material in the graphene-based selection process is removed, and a target specific aptamer is separated from the graphene by causing a conformational by the target material on a target specific single-stranded nucleic acid bound to the graphene.

Further, the present invention provides a nucleic acid aptamer having a sequence selected from the group consisting of the base sequences set forth in SEQ ID NOS: 4 to 18 in which the nucleic acid aptamer is specifically bound to a Nampt protein.

Furthermore, the present invention provides a composition for detecting a Nampt protein comprising: a nucleic acid aptamer having a sequence selected from the group consisting of the base sequences set forth in SEQ ID NOS: 4 to 18 in which the nucleic acid aptamer is specifically bound to a Nampt protein.

Moreover, the present invention provides a composition for diagnosing a Nampt related disease comprising: a nucleic acid aptamer having a sequence selected from the group consisting of the base sequences set forth in SEQ ID NOS: 4 to 18 in which the nucleic acid aptamer is specifically bound to a Nampt protein.

Also, the present invention provides a solid phase carrier immobilizing a nucleic acid aptamer having a sequence selected from the group consisting of the base sequences set forth in SEQ ID NOS: 4 to 18 in which the nucleic acid aptamer is specifically bound to a Nampt protein.

Further, the present invention provides a kit for detecting a Nampt protein comprising: a nucleic acid aptamer having a sequence selected from the group consisting of the base sequences set forth in SEQ ID NOS: 4 to 18 in which the nucleic acid aptamer is specifically bound to a Nampt protein.

Furthermore, the present invention provides a kit for diagnosing a Nampt related disease comprising: a nucleic acid aptamer having a sequence selected from the group consisting of the base sequences set forth in SEQ ID NOS: 4 to 18 in which the nucleic acid aptamer is specifically bound to a Nampt protein.

Moreover, the present invention provides a composition for separating a Nampt protein comprising: a nucleic acid aptamer having a sequence selected from the group consisting of the base sequences set forth in SEQ ID NOS: 4 to 18 in which the nucleic acid aptamer is specifically bound to a Nampt protein.

Also, the present invention provides a Nampt protein separation method comprising: bringing a Nampt protein-containing sample in contact with a solid phase carrier immobilizing a nucleic acid aptamer having a sequence selected from the group consisting of the base sequences set forth in SEQ ID NOS: 4 to 18 in which the nucleic acid aptamer is specifically bound to a Nampt protein; and eluting the Nampt protein bound to the solid phase carrier using an eluent.

Further, the present invention provides a nucleic acid aptamer having a sequence selected from the group consisting of the base sequences set forth in SEQ ID NOS: 19 to 28 in which the nucleic acid aptamer is specifically bound to a Bovine Viral Diarrhea Virus type 1.

Furthermore, the present invention provides a composition for detecting a Bovine Viral Diarrhea Virus type 1 comprising: a nucleic acid aptamer having a sequence selected from the group consisting of the base sequences set forth in SEQ ID NOS: 19 to 28 in which the nucleic acid aptamer is specifically bound to a Bovine Viral Diarrhea Virus type 1.

Moreover, the present invention provides a Bovine Viral Diarrhea Virus type 1 detection method comprising: bringing a nucleic acid aptamer having a sequence selected from the group consisting of the base sequences set forth in SEQ ID NOS: 19 to 28 in which the nucleic acid aptamer is specifically bound to a Bovine Viral Diarrhea Virus type 1 in contact with a Bovine Viral Diarrhea Virus type 1-containing sample to detect the Bovine Viral Diarrhea Virus type 1.

Also, the present invention provides a composition for diagnosing bovine viral diarrhea comprising: a nucleic acid aptamer having a sequence selected from the group consisting of the base sequences set forth in SEQ ID NOS: 19 to 28 in which the nucleic acid aptamer is specifically bound to a Bovine Viral Diarrhea Virus type 1.

Further, the present invention provides a solid phase carrier immobilizing a nucleic acid aptamer having a sequence selected from the group consisting of the base sequences set forth in SEQ ID NOS: 19 to 28 in which the nucleic acid aptamer is specifically bound to a Bovine Viral Diarrhea Virus type 1.

Furthermore, the present invention provides a kit for detecting a Bovine Viral Diarrhea Virus type 1 comprising: a nucleic acid aptamer having a sequence selected from the group consisting of the base sequences set forth in SEQ ID NOS: 19 to 28 in which the nucleic acid aptamer is specifically bound to a Bovine Viral Diarrhea Virus type 1.

Moreover, the present invention provides a kit for diagnosing bovine viral diarrhea comprising: a nucleic acid aptamer having a sequence selected from the group consisting of the base sequences set forth in SEQ ID NOS: 19 to 28 in which the nucleic acid aptamer is specifically bound to a Bovine Viral Diarrhea Virus type 1.

Also, the present invention provides a composition for separating a Bovine Viral Diarrhea Virus type 1 comprising: a nucleic acid aptamer having a sequence selected from the group consisting of the base sequences set forth in SEQ ID NOS: 19 to 28 in which the nucleic acid aptamer is specifically bound to a Bovine Viral Diarrhea Virus type 1.

In addition, the present invention provides a Bovine Viral Diarrhea Virus type 1 separation method comprising: bringing a Bovine Viral Diarrhea Virus type 1-containing sample in contact with a solid phase carrier immobilizing a nucleic acid aptamer having a sequence selected from the group consisting of the base sequences set forth in SEQ ID NOS: 19 to 28 in which the nucleic acid aptamer is specifically bound to a Bovine Viral Diarrhea Virus type 1; and eluting the Bovine Viral Diarrhea Virus type 1 bound to the solid phase carrier using an eluent.

BRIEF DESCRIPTION OF THE DRAWINGS

The above and other objects, features, and advantages of the present invention will become more apparent to those of ordinary skill in the art by describing in detail exemplary embodiments thereof with reference to the attached drawings, in which:

FIG. 31 illustrates a result of binding specificity of an aptamer B1-11 (SEQ ID NO: 23), an aptamer B1-34 (SEQ ID NO: 21), and an aptamer B1-43 (SEQ ID NO: 26) as aptamers specific to a BVDV type 1 to the BVDV type 1 (BVDV t1) and similar substances (BVDV type 2, CSFV, MDBK, and BSA) according to the present invention.

FIG. 32 is a graph showing affinity of an aptamer B1-11 (SEQ ID NO: 23), an aptamer B1-34 (SEQ ID NO: 21), and an aptamer B1-43 (SEQ ID NO: 26) as aptamers specific to a BVDV type 1 to the BVDV type 1.

FIG. 33 provides a schematic diagram of a detection method using a sandwich method according to the present invention.

FIG. 34 illustrates a result of binding force when an aptamer B1-11 (SEQ ID NO: 23) having the lowest $K_d$ among aptamers specific to a BVDV type 1 is immobilized and an aptamer B1-43 (SEQ ID NO: 26) having the highest $K_d$ is reacted in a second-order reaction.

DETAILED DESCRIPTION OF EXEMPLARY EMBODIMENTS

Figure 1:
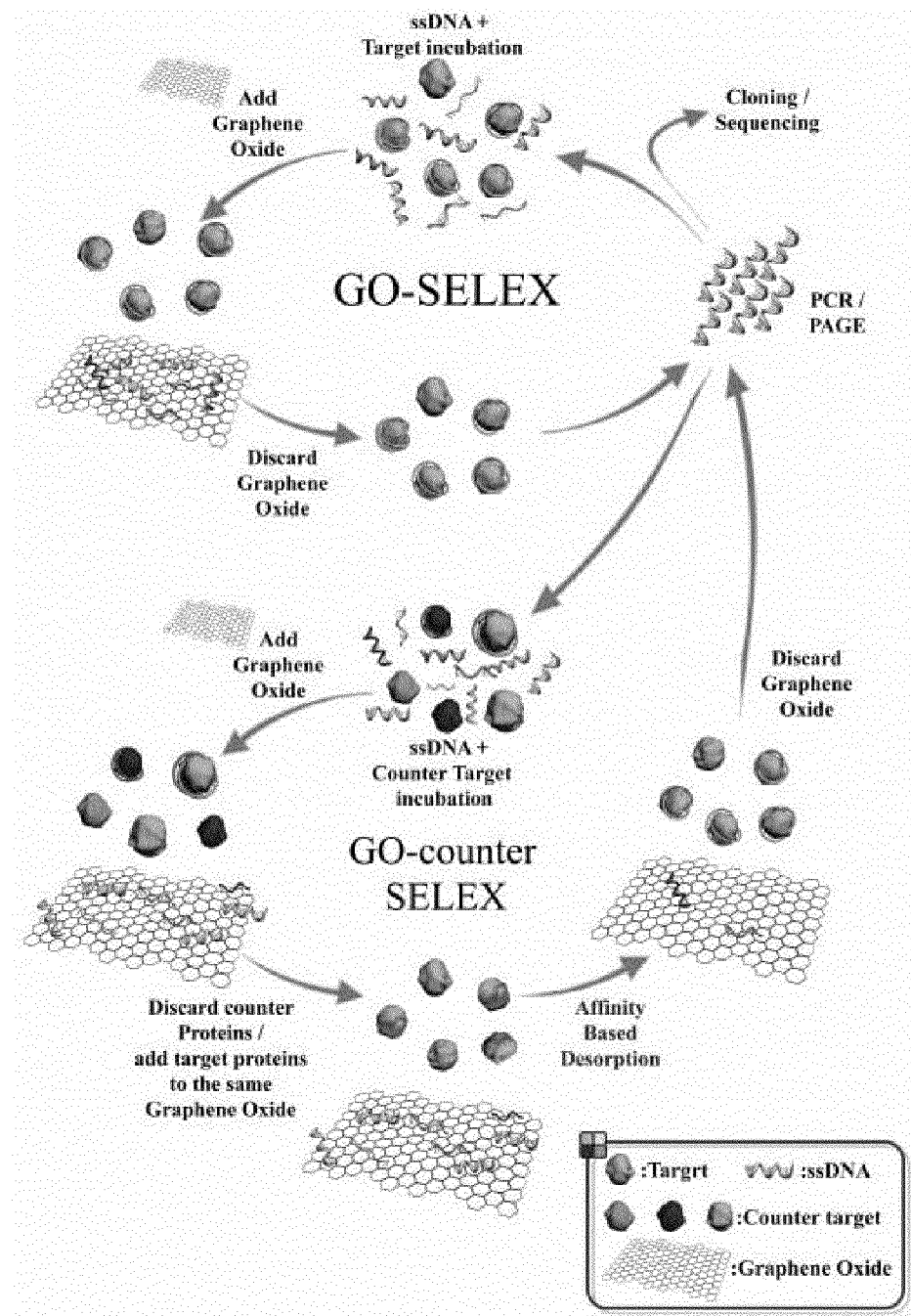
FIG. 1 provides a schematic diagram of a single-stranded nucleic acid aptamer development method using a graphene oxide (GO-SELEX) according to the present invention.

Hereinafter, exemplary embodiments of the present invention will be described in detail. However, the present invention is not limited to the embodiments disclosed below, but can be implemented in various forms. The following embodiments are described in order to enable those of ordinary skill in the art to embody and practice the present invention.

Although the terms first, second, etc. may be used to describe various elements, these elements are not limited by these terms. These terms are only used to distinguish one element from another. For example, a first element could be termed a second element, and, similarly, a second element could be termed a first element, without departing from the scope of exemplary embodiments. The term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

The terminology used herein is for the purpose of describing particular embodiments only and is not intended to be limiting of exemplary embodiments. The singular forms "a," "an," and "the" are intended to include the plural forms as well, unless the context clearly indicates otherwise. It will be further understood that the terms "comprises," "comprising," "includes," and/or "including," when used herein, specify the presence of stated features, integers, steps, operations, elements, components, and/or groups thereof, but do not preclude the presence or addition of one or more other features, integers, steps, operations, elements, components, and/or groups thereof.

With reference to the appended drawings, exemplary embodiments of the present invention will be described in detail below. To aid in understanding the present invention, like numbers refer to like elements throughout the description of the figures, and the description of the same elements will be not reiterated.

The main terms used in the detailed description of the present invention will be defined as follows.

The term "nucleic acid aptamer" refers to a small single-stranded oligonucleotide that can specifically recognize its target material with high affinity. Nucleic acid aptamers are offered as single-stranded DNA or RNA. Therefore, if the nucleic acid is RNA, T in a sequence of the nucleic acid is expressed as U. It is obvious to one of ordinary skill in the art that such a sequence is included in the scope of the present invention.

The terms "graphene," "graphene oxide," "graphene oxide nanosheet," and "graphene nanosheet" mean two-dimensional carbon structures and may be used interchangeably throughout the present specification.

The term "sample" refers to a composition that contains or is assumed to contain a target material, for example, a protein, a low molecular material, a virus, etc., and will be analyzed and may be detected from a sample collected from any one or more of, but not limited to, liquid, soil, air, food, waste, animal intestines, and animal tissues. Herein, the liquid may be serum, blood, urine, water, tears, sweat, saliva, lymph, and cerebrospinal fluid. The water may include river water, seawater, lake water, and rain water. The waste may include sewage, waste water, and the like. The animal may include a cow. Further, the animal tissues may include mucous membranes, skin, cortices, hair, scales, eyes, tongues, cheeks, hooves, beaks, snouts, feet, hands, mouths, nipples, ears, noses, etc.

The term "counter-target material" or "counter target" comprehensively means a material belonging to a family which has a similar structure, a similar active site, or similar activity to a target or a target material. For example, if a target material is a Nampt protein, adiponectin, RBP4 (Retinol Binding Protein 4), resistin, vaspin, and HSA (Human Serum Albumin) may be used as a counter-target material. If a target material is a Bovine Viral Diarrhea Virus type 1, Bovine Viral Diarrhea Virus type 2 (BVDV type 2), CSFV (Classical Swine Fever Virus), MDBK (Mardin-Darby Bovine Kidney cell), or BSA (Bovine Serum Albumin) may be used as a counter-target material.

One aspect of the present invention relates to a method for producing a nucleic acid aptamer without target immobilization comprising: reacting a single-stranded nucleic acid pool including a PCR primer region at both ends and any 30 to 50 bases at its center with a target material or a counter-target material and adding graphene; and separating a target specific nucleic acid aptamer by removing a target non-specific single-stranded nucleic acid bound to the graphene, or separating a target specific nucleic acid aptamer from the graphene by causing a conformational change by the target material on a target specific single-stranded nucleic acid bound to the graphene.

As a general method for developing an aptamer selectively bound to a target, a SELEX (Systematic Evolution of Ligand by Exponential Enrichment) method has been widely used. In the present invention, a nucleic acid aptamer specifically bound to a target material is developed using a graphene oxide (GO)-SELEX method modified from the general SELEX method.

The GO-SELEX method used in the present invention is the SELEX method using graphene oxide to distinguish a nucleic acid which is bound or not bound to a target or a counter target, and the GO-SELEX method uses a fluorescence labeled primer during a nucleic acid amplification step, and thus, during a subsequent PCR product separation (for example, dsDNA→ssDNA) step using PAGE, it is necessary to take out only a fluorescent band. In the conventional SELEX methods, a radioactive label, capillary electrophoresis, a membrane filter, etc. have been used, but such methods require great expense and are difficult to handle. One of the core parts of the SELEX method is to separate a nucleic acid which is bound to a target material from a nucleic acid which is not bound to the target material. In order to separate them, chromatography, an affinity column, and the like have been used, but they are expensive and less efficient (R. Stoltenburg et al., 2005, Anal Bioanal Chem 383: 83-91). However, the present invention is characterized in that since a single-stranded nucleic acid which is not bound to a target material or a counter-target material is removed using graphene, even if the target material or the counter-target material is not specifically immobilized to a specific carrier, it is possible to separate a single-stranded nucleic acid which is bound to the target material or the counter-target material from the single-stranded nucleic acid which is not bound to the target material or the counter-target material. By this method, it is possible to simply and easily solve the problems of the conventional target immobilizing methods. The present invention can employ the typical target immobilizing SELEX method as it is except that a single-stranded nucleic acid which is not bound to a target material or a counter-target material is removed using graphene.

The method for producing nucleic acid aptamer without target immobilization of the present invention may further comprise amplifying a single-stranded nucleic acid specifically bound to the target material by performing a PCR using the PCR primer region on the single-stranded nucleic acid separated from the target material/single-stranded nucleic acid complex in order to increase an amount of the single-stranded nucleic acid.

In the method for producing a nucleic acid aptamer without target immobilization, selection of the target specific aptamer is carried out by, for example, repeatedly carrying out a graphene-based selection process and a counter selection process one or more times using the target material and the counter-target material with respect to a single-stranded nucleic acid specifically bound to the target material.

Herein, by the graphene-based counter selection process, it is possible to remove a target non-specific single-stranded nucleic acid bound to the counter target material and select a single-stranded nucleic acid which is not bound to the counter target material but bound to the graphene.

Although not limited hereto, as a method for separating the single-stranded nucleic acid, which is not bound to a counter-target material but bound to graphene, from the graphene, a method for separating a target specific aptamer from graphene by causing a conformational change by a main target with respect to a single-stranded nucleic acid bound to graphene may be used.

Each step of the method for producing a nucleic acid aptamer without target immobilization of the present invention will be explained in detail as follows with reference to FIG. 1.

In a first step, a single-stranded nucleic acid pool including a PCR primer region at both ends and any 30 to 50 bases at its center is mixed with a target material or a counter-target material in a buffer solution, and these are induced to be bound to each other at normal temperature.

To be more specific, a nucleic acid pool of approximately 66 mers including binding sites (about 18 mers each) of a primer for PCR amplification at both ends and about 30 bases at its center is synthesized, and the nucleic acid pool is mixed with a target material or a counter-target material in a buffer solution to make a binding reaction.

The single-stranded nucleic acid pool may include, but is not particularly limited to, a primer region set forth in SEQ ID NO: 1 at its 5' end and a primer region set forth in SEQ ID NO: 2 at its 3' end.

The target material may include, but is not particularly limited to, a protein such as a Nampt protein having a molecular weight of 5000 to 500000 daltons, a low molecular material having a molecular weight of 10 to 2000 daltons, or a virus such as Bovine Viral Diarrhea Virus type 1.

The counter-target material may be a substance structurally and functionally similar to the target material and may be appropriately selected and used depending on a kind of the target material without particular limitation. For example, if the target material is a Nampt protein, similar substances such as adiponectin, RBP4 (Retinol Binding Protein 4), resistin, vaspin, and HSA (Human Serum Albumin) may be used. If the target material is a Bovine Viral Diarrhea Virus type 1, similar substances such as Bovine Viral Diarrhea Virus type 2 (BVDV type 2), CSFV (Classical Swine Fever Virus), MDBK (Mardin-Darby Bovine Kidney cell), or BSA (Bovine Serum Albumin) may be used.

In a second step, the mixture is reacted with graphene to remove a single-stranded nucleic acid which is not bound to the target material or the counter-target material.

If graphene is added to a mixture of the single-stranded nucleic acid pool and the target material, a target non-specific single-stranded nucleic acid which is not bound to the target material is bound to the graphene and thus removed by centrifugation, and a supernatant including a target material/single-stranded nucleic acid complex is taken to obtain a nucleic acid bound to the target by an ethanol precipitation method.

If graphene is added to a mixture of the single-stranded nucleic acid pool and the counter-target material, a target specific single-stranded nucleic acid which is not bound to the counter-target material is bound to the graphene. Therefore, a target specific nucleic acid aptamer is separated from the graphene by causing a conformational change by the target with respect to the target specific single-stranded nucleic acid bound to the graphene.

In a third step, a single-stranded nucleic acid specifically bound to the target material and obtained in the above step is amplified by performing a PCR using the PCR primer region.

A PCR is performed to amplify the single-stranded nucleic acid specifically bound to the target material, a PCR product is purified, and then electrophoresis is carried out with polyacrylamide gel containing a high concentration of urea to separate the PCR product as a double-stranded nucleic acid into two single-stranded nucleic acids. In this case, since the PCR product is a double-stranded nucleic acid, a label is immobilized to a primer in order to perform a denaturation process for separating the double-stranded nucleic acid into single-stranded nucleic acids. During the electrophoresis, the double-stranded nucleic acid is denatured, and a nucleic acid strand with the label and a nucleic acid strand without the label are positioned up and down, respectively. The nucleic acid band with the label is cut off and extracted from the polyacrylamide gel, and then the separated nucleic acid is obtained by performing the ethanol precipitation method again.

A primer pair for the PCR may be set forth in SEQ ID NOS: 1 and 3, but is not particularly limited thereto.

The label may be a fluorescent material such as, but not particularly limited to, Cy5, Alexa Fluor 350, Alexa Fluor 430, Alexa Fluor 488, Alexa Fluor 532, Alexa Fluor 546, Alexa Fluor 594, Alexa Fluor 658, Cyanine-3, Cyanine-5, fluorescein, bodipy, Texas red, FITC (Fluorescein Isothiocyanate), rhodamine, or the like.

In a fourth step, a graphene-based selection process and a counter selection process are carried out repeatedly one or more times on the single-stranded nucleic acid specifically bound to the target material using the target material and the counter-target material.

The single-stranded nucleic acid pool specifically bound to the target material and obtained in the above step is reacted with the target material to increase affinity and a binding property with respect to the target. The selection process including a series of processes is carried out several times. Then, the counter selection process is carried out by using the counter-target material to block a nucleic acid which is not specifically bound to the counter-target material. Thus, a nucleic acid pool specifically bound to the target material only with high affinity is obtained through the selection process and the counter selection process.

In the counter selection process, if graphene is added after the counter target material is reacted with the nucleic acid pool, a single-stranded nucleic acid which is not bound to the counter-target material is adsorbed onto a surface of the graphene.

In a fifth step, a target non-specific single-stranded nucleic acid bound to the counter-target material in the graphene-based selection process is removed, and a target specific aptamer is separated from the graphene by causing a conformational change by the target material through a reaction between a target specific single-stranded nucleic acid bound to the graphene and the target.

As for a single-stranded nucleic acid which is not bound to the counter-target material, a supernatant is removed by centrifugation and only graphene is taken out to obtain a single-stranded nucleic acid adsorbed onto the graphene from the graphene. To do so, the target material is reacted on the surface of the graphene onto which the single-stranded nucleic acid is adsorbed, and the target material causes a conformational change of the single-stranded nucleic acid adsorbed onto the graphene to effectively separate the single-stranded nucleic acid from the surface of the graphene. The single-stranded nucleic acid separated as such becomes a candidate for an aptamer which is not bound to a counter target but strongly bound to a main target material.

The candidate for an aptamer is cloned using a cloning vector such as a pDrive Cloning Vector (Qiagen, Netherlands), and a nucleic acid is extracted from a resultant colony to carry out a base sequence analysis.

In a method for comparing specific binding capacities of an aptamer specifically bound to a target with respect to other proteins and magnitudes of binding force depending on a concentration of a target material, a surface magnetic resonance device (SPR) may be used. To do so, a surface of a bare gold chip is modified and each DNA aptamer is immobilized onto the chip. Then, a target material is reacted thereon at various concentrations and binding force thereof is checked and also binding force with respect to other counter-target materials is tested for analyzing specific binding capacities.

A nucleic acid aptamer having a high target binding force is selected to be used for detecting and separating the target.

A nucleic acid aptamer selected by the method for producing nucleic acid aptamer without target immobilization of the present invention may include a nucleic acid aptamer having a sequence selected from the group consisting of the base sequences set forth in SEQ ID NOS: 4 to 28 in which the nucleic acid aptamer can be specifically bound to a Nampt protein or a Bovine Viral Diarrhea Virus type 1, but is not particularly limited thereto since it may vary depending on a kind of a target.

According to another aspect of the present invention, the present invention provides a specific aptamer selected by the method for producing a nucleic acid aptamer without target immobilization and a use thereof.

Therefore, the present invention relates to a nucleic acid aptamer having a sequence selected from the group consisting of the base sequences set forth in SEQ ID NOS: 4 to 18 in which the nucleic acid aptamer is specifically bound to a Nampt protein.

The aptamer of the present invention is selected to target a Nampt protein, and the Nampt protein may be that of a mammal such as a human or a mouse, and more preferably, may be extracellular human Nampt protein (visfatin/PBEF) and may include amino acid sequences of 1 to 491.

Further, the Nampt protein used as a target may include a peptide synthesized by a publicly known method for synthesizing peptides, a commercially available Nampt protein such as a Nampt protein (Prod. No. AG-40A-0031) of AdipoGen Inc., and a whole or a part of the Nampt protein expressed from a recombinant vector manufactured by introducing a coding gene of the protein into a vector (for example, pAGNF, etc.), but is not particularly limited thereto.

Further, the expression "specifically bound to a Nampt protein" means being specifically bound to the Nampt protein defined above by a covalent bond or a noncovalent bond.

The nucleic acid aptamer may be a DNA aptamer which is selected by the GO-SELEX method and specifically bound to a Nampt protein and has a certain base sequence, and preferably, a sequence selected from the group consisting of the base sequences set forth in SEQ ID NOS: 4 to 18.

The aptamer of the present invention can be chemically synthesized by a method publicly known in the art.

The aptamer of the present invention may include a modified glycosyl unit (for example, ribose or dioxyribose) of each nucleotide to increase a binding capacity with respect to a Nampt protein, stability, etc. At a modified site in the glycosyl unit, an oxygen atom at, for example, a 2' site, a 3' site, and/or a 4' site in the glycosyl unit may be substituted with other atoms. The modification may include, for example, fluorination, O-alkylation (for example, O-methylation and O-ethylation), O-allylation, S-alkylation (for example, S-methylation and S-ethylation), S-allylation, and amination (for example, —NH). Such modification of the glycosyl unit is carried out by a publicly known method (for example, refer to Sproat et al., (1991) *Nucle. Acid. Res.* 19, 733-738; Cotton et al., (1991) *Nucl. Acid. Res.* 19, 2629-2635; Hobbs et al., (1973) *Biochemistry* 12, 5138-5145).

The aptamer of the present invention may include a modified (for example, chemically substituted) nucleic acid base (for example, purine and pyrimidine) to increase a binding capacity with respect to a Nampt protein, and the like. The modification may include, for example, 5-position pyrimidine modification, 6- and/or 8-position purine modification, modification at an exocyclic amine, substitution with 4-thiouridine, and substitution with 5-bromo- or 5-iodo-uricyl.

Further, a phosphate group contained in the aptamer of the present invention may be modified to be resistant to nuclease and hydrolysis. For example, the P(0)0 group may be substituted with P(0)S (thioate), P(S)S (dithioate), P(0)NR$_2$ (amidate), P(0)R, P(0)OR', CO or CH$_2$ (formacetal) or 3'-amine (—NH—CH$_2$—CH$_2$—). Herein, each R or R' is independently H or a substituted or unsubstituted alkyl (for example, methyl and ethyl). Linkage groups may be —O—, —N—, or —S— linkage and can be bonded to adjacent nucleotides through the —O—, —N—, or —S— linkage.

The modification of the present invention may further include 3' and 5' modifications such as capping.

Further, the modification may be carried out by adding polyethylene glycol, an amino acid, a peptide, inverted dT, a nucleic acid, a nucleoside, myristoyl, lithocolic-oleyl, docosanyl, lauroyl, stearoyl, palmitoyl, oleoyl, linoleoyl, other lipids, a steroid, cholesterol, caffeine, a vitamin, a pigment, a fluorescent material, an anti-cancer drug, a toxin, an enzyme, a radioactive material, biotin, etc. to an end. Regarding such modifications, refer to, for example, U.S. Pat. No. 5,660,985 and U.S. Pat. No. 5,756,703.

The present invention further relates to a composition for detecting a Nampt protein comprising: a nucleic acid aptamer having a sequence selected from the group consisting of the base sequences set forth in SEQ ID NOS: 4 to 18 in which the nucleic acid aptamer is specifically bound to a Nampt protein.

Furthermore, the present invention relates to a method for detecting a Nampt protein comprising: bringing the nucleic acid aptamer in contact with a Nampt protein-containing sample to detect the Nampt protein.

Using a formation of a complex of the aptamer of the present invention and a Nampt protein by a covalent bond or a noncovalent bond, it is possible to detect the Nampt protein. The detection can be carried out by the same method as the immunological method except that the aptamer of the present invention is used instead of an antibody. Therefore, using the aptamer of the present invention instead of an antibody, detection and quantitation can be carried out by a method such as an enzyme immune-assay (EIA) (for example, competitive direct ELISA, competitive indirect ELISA, and sandwich ELISA), a radioimmuno assay (RIA), a fluorescence immuno assay (FIA), western blotting (for example, used as a secondary antibody in western blotting), an immunohistochemical staining method, a cell sorting method, etc.

The present invention further relates to a composition for diagnosing a Nampt related disease comprising: a nucleic acid aptamer having a sequence selected from the group consisting of the base sequences set forth in SEQ ID NOS: 4 to 18 in which the nucleic acid aptamer is specifically bound to a Nampt protein.

The Nampt related disease may include, for example, type 2 diabetes, colorectal cancer, prostate cancer, breast cancer, stomach cancer, polycystic ovarian syndrome, chronic renal failure, or chronic obstructive lung disease.

Diagnosis of the Nampt related disease may comprise bringing the aptamer in contact with a sample selected from tissue, cells, blood, serum, plasma, saliva, sputum, and urine. It is obvious that the sample is not limited to the above-described examples as long as it is separated from a mammal, preferably a human, and contains Nampt as a biomarker such as a sample obtained by minimal invasion or a secretory body fluid sample, an in vitro cell culture medium sample, etc. More preferably, the sample may be blood. For diagnosis of the Nampt related diseases, it is very important to accurately measure a concentration of Nampt as an important biomarker for the Nampt related diseases in blood. Therefore, the composition containing the nucleic acid aptamer of the present invention which is not specific to other various biomaterials in a blood sample but can be specifically bound to Nampt even in a small amount can be used to diagnose the Nampt related diseases more rapidly and accurately.

If the aptamer is brought in contact with the sample, a specific bond is formed between Nampt as a biomarker present in the sample and the aptamer. Therefore, it is possible to detect a Nampt related disease by labeling the aptamer with fluorescence and allowing the aptamer to be bound, and checking whether there is a signal or not.

The present invention further relates to a solid phase carrier immobilizing a nucleic acid aptamer having a sequence selected from the group consisting of the base sequences set forth in SEQ ID NOS: 4 to 18 in which the nucleic acid aptamer is specifically bound to a Nampt protein.

The solid phase carrier may include a substrate, a resin, a plate (for example, a multiwall plate), a filter, a cartridge, a column, or a porous material.

The substrate may be employed from one used in a DNA chip or a protein chip and may include, for example, a nickel-PTFE (polytetrafluoroethylene) substrate, a glass substrate, an apatite substrate, a silicon substrate, a gold substrate, a silver substrate, or an alumina substrate, and a polymer or the like may be coated on the substrate.

The resin may include agarose particles, silica particles, a copolymer of acrylamide and N,N'-methylenebisacrylamide, polystyrene-crosslinked divinylbenzene particles, epichlorohydrin-crosslinked dextran particles, a cellulose fiber, a crosslinked polymer of allyldextran and N,N'-methylenebisacrylamide, a monodispersed synthetic polymer, a monodispersed hydrophilic polymer, sepharose or Toyopearl, and the resin may be bonded to various functional groups.

The solid phase carrier can be used to separate, purify, detect or quantitate the Nampt protein.

The aptamer of the present invention may be immobilized to a solid phase carrier by a publicly known method. For example, a method in which an affinity substance or a certain functional group is introduced into the aptamer of the present invention and the affinity substance or the certain functional group is immobilized to a solid phase carrier may be used.

The certain functional group may be a functional group which can be provided in a coupling reaction, and may include, for example, an amino group, a thiol group, a hydroxyl group, and a carboxyl group. For example, biotin may be bound to an end of the aptamer to form a complex, and streptavidin may be immobilized to a surface of a substrate such as a chip, and thus the aptamer can be immobilized to the surface of the substrate by an interaction between the biotin and the streptavidin immobilized to the surface of the substrate.

In a method for detecting a Nampt protein using a solid phase carrier immobilizing an aptamer, for example, the nucleic acid aptamer of the present invention is spotted on a chip together with a fluorescent material, a staining material, or an antibody and then reacts with a blood sample, whereby it is possible to rapidly measure a detection sample, for example, a trace of Nampt contained in the blood. In another method, if Nampt is bound to magnetic beads by immobilizing the nucleic acid aptamer to the magnetic beads, the bound nucleic acid aptamer/Nampt complex can be separated using a magnet, and Nampt only can be selectively detected by again separating Nampt from the complex. In addition to the methods described in the exemplary embodiments of the present invention, a method in which Nampt in blood can be detected using a sensor linked with the nucleic acid aptamer of the present invention by a linkage may be used.

The detection of the Nampt protein using the solid phase carrier can be used to diagnose Nampt related diseases.

Further, the present invention can be provided in the form of a kit for detecting a Nampt protein or a kit for diagnosing a Nampt related disease comprising: a nucleic acid aptamer having a sequence selected from the group consisting of the base sequences set forth in SEQ ID NOS: 4 to 18 in which the nucleic acid aptamer is specifically bound to a Nampt protein.

The kit may include, if necessary, a buffer solution and containers for detection and analysis in the form of bottles, tubs, sachets, envelopes, tubes, ampoules, etc. which may be partially or entirely made of plastic, glass, paper, foil, wax, etc. The container may be equipped with a stopper which may be a part of the container or can be attached to the container mechanically or by means of adhesion or other means and can be entirely or partially detached from the container. Further, the container may be equipped with a stopper which can approach the contents via an injection needle. The kit may include an exterior package, and the exterior package may include an instruction manual about use of the components.

The aptamer specifically bound to a Nampt protein according to the present invention specifically detects the Nampt protein only. Therefore, it is obvious to one of ordinary skill in the art that a composition for separating the Nampt protein comprising the same can be provided.

Therefore, the present invention provides a composition for separating a Nampt protein comprising: a nucleic acid aptamer having a sequence selected from the group consisting of the base sequences set forth in SEQ ID NOS: 4 to 18 in which the nucleic acid aptamer is specifically bound to a Nampt protein.

Further, the present invention provides a Nampt protein separation method comprising: bringing a Nampt protein-containing sample in contact with a solid phase carrier immobilizing a nucleic acid aptamer having a sequence selected from the group consisting of the base sequences set forth in SEQ ID NOS: 4 to 18 in which the nucleic acid aptamer is specifically bound to a Nampt protein; and eluting the Nampt protein bound to the solid phase carrier using an eluent.

The Nampt protein can be bound to the solid phase carrier of the present invention by a publicly known method. For example, a Nampt protein-containing sample (for example, bacteria, a culture or a culture supernatant of cells, or blood) may be introduced to the solid phase carrier of the present invention or another material containing the same.

The elution of the Nampt protein can be carried out using an eluent such as a neutral solution. A neutral eluent is not particularly limited and may have, for example, a pH of about 6 to about 9, preferably about 6.5 to about 8.5, and more preferably about 7 to about 8. The neutral solution may contain potassium salts (for example, NaCl and KCl), magnesium salts (for example, MgCl), surfactants (for example, Tween 20, Triton, and NP40), or glycerin.

The separation method of the present invention may comprise a process for cleaning the solid phase carrier with a cleaning solution after the Nampt protein is bound. The cleaning solution may include urea, a chelate agent (for example, EDTA), Tris, an acid, or an alkali.

The separation method of the present invention may comprise a process for heating the solid phase carrier. Through this process, the solid phase carrier can be regenerated and sterilized.

According to another aspect of the present invention, the present invention relates to a nucleic acid aptamer having a sequence selected from the group consisting of the base sequences set forth in SEQ ID NOS: 19 to 28 in which the nucleic acid aptamer is specifically bound to a Bovine Viral Diarrhea Virus type 1.

The aptamer of the present invention is selected by the GO-SELEX method to target a Bovine Viral Diarrhea Virus type 1 and may be a DNA aptamer which is specifically bound to the virus and has a certain base sequence, and preferably a sequence selected from the group consisting of the base sequences set forth in SEQ ID NOS: 19 to 28.

The aptamer of the present invention can be chemically synthesized by a method publicly known in the art.

The aptamer of the present invention may include a modified glycosyl unit (for example, ribose or dioxyribose) of each nucleotide to increase a binding capacity with respect to a Bovine Viral Diarrhea Virus type 1, stability, etc. A modified site in the glycosyl unit, a kind of modification, and a modification method of the glycosyl unit are the same as described above.

The aptamer of the present invention may include a modified (for example, chemically substituted) nucleic acid base (for example, purine and pyrimidine) to increase a binding capacity with respect to a Bovine Viral Diarrhea Virus type 1, and the like. A kind of this modification is the same as described above.

Further, a phosphate group contained in the aptamer of the present invention may be modified to be resistant to nuclease and hydrolysis. A kind of this modification is the same as described above.

The modification of the present invention may further include 3' and 5' modifications such as capping. A kind of this modification is the same as described above.

The present invention further relates to a composition for detecting a Bovine Viral Diarrhea Virus type 1 comprising: a nucleic acid aptamer having a sequence selected from the group consisting of the base sequences set forth in SEQ ID NOS: 19 to 28 in which the nucleic acid aptamer is specifically bound to a Bovine Viral Diarrhea Virus type 1.

Furthermore, the present invention relates to a method for detecting a Bovine Viral Diarrhea Virus type 1 comprising: bringing the nucleic acid aptamer having a sequence selected from the group consisting of the base sequences set forth in SEQ ID NOS: 19 to 28 in which the nucleic acid aptamer is specifically bound to a Bovine Viral Diarrhea Virus type 1 in contact with a Bovine Viral Diarrhea Virus type 1-containing sample to detect the Bovine Viral Diarrhea Virus type 1.

The Bovine Viral Diarrhea Virus type 1 may be detected from a sample collected from any one of serum, blood, urine, water, tears, sweat, saliva, lymph, cerebrospinal fluid, soil, air, food, waste, animal intestines, and animal tissues, but is not limited thereto. Herein, the water may include river water, seawater, lake water, and rain water. The waste may include sewage, wastewater, and the like. The animal may include a cow. Further, the animal tissues may include mucous membranes, skin, cortices, hair, scales, eyes, tongue, cheeks, hooves, beaks, snouts, feet, hands, mouths, nipples, ears, noses, etc.

According to an exemplary embodiment of the present invention, as a result of comparing binding capacity of an aptamer specific to a Bovine Viral Diarrhea Virus type 1 (BVDV type 1) and a magnitude of binding force depending on a concentration of the BVDV type 1 using a surface magnetic resonance device (SPR), the aptamer was found to exhibit a very high binding force with respect to the BVDV type 1 (BVDV t1) but not to bind well to other similar substances (CSFV, MDBK, and BSA) including BVDV type 2 (BVDV t2). Such a result means that the nucleic acid aptamer specific to the BVDV type 1 of the present invention can specifically detect the BVDV type 1 and also enables bovine viral diarrhea to be diagnosed more accurately.

Therefore, the present invention relates to a composition for diagnosing bovine viral diarrhea comprising: a nucleic acid aptamer having a sequence selected from the group consisting of the base sequences set forth in SEQ ID NOS: 19 to 28 in which the nucleic acid aptamer is specifically bound to a Bovine Viral Diarrhea Virus type 1.

The diagnosis of bovine viral diarrhea is carried out to diagnose bovine viral diarrhea of animals other than humans, particularly cows.

Further, the nucleic acid aptamer specific to a BVDV type 1 of the present invention can be used to detect the BVDV type 1 or to diagnose bovine viral diarrhea by a sandwich binding method using a first aptamer and a second aptamer. For example, it is possible to detect a BVDV type 1 or diagnose bovine viral diarrhea by bringing a Bovine Viral Diarrhea Virus type 1-containing sample in contact with a solid phase carrier immobilizing a first nucleic acid aptamer specific to the Bovine Viral Diarrhea Virus type 1, adding a second nucleic acid aptamer specific to the Bovine Viral Diarrhea Virus type 1 to detect whether or not a sandwich complex of the first nucleic acid aptamer, the Bovine Viral Diarrhea Virus type 1, and the second nucleic acid aptamer is formed.

The first nucleic acid aptamer is immobilized to the solid phase carrier and used to be bound to the Bovine Viral Diarrhea Virus type 1-containing sample and may have a base sequence set forth in SEQ ID NOS: 23, but any aptamer specific to the Bovine Viral Diarrhea Virus type 1 can be used without limitation.

The second nucleic acid aptamer can be used to be bound to a complex of the first nucleic acid aptamer and the Bovine Viral Diarrhea Virus type 1, and since it is bound to a label selected from the group consisting of a fluorescent material, a quantum dot, a radioactive label, a gold nanoparticle, an enzyme, an enzyme-substrate, and a electrochemical functional group, it is possible to detect whether or not the sandwich complex of the first nucleic acid aptamer, the Bovine Viral Diarrhea Virus type 1, and the second nucleic acid aptamer is formed by detecting the label or a reaction of the label so as to detect the BVDV type 1 or diagnose bovine viral diarrhea.

The second nucleic acid aptamer may have a base sequence set forth in SEQ ID NOS: 26, but any aptamer specific to the Bovine Viral Diarrhea Virus type 1 can be used without limitation.

Any signal processing method may be used to check whether or not the sandwich complex of the first nucleic acid aptamer, the Bovine Viral Diarrhea Virus type 1, and the second nucleic acid aptamer is formed as long as it can check a complex, and it can be appropriately used depending on, for example, a kind of a label.

The detection of the label or a reaction of the label may be carried out by a generally known method for analyzing a label or a reaction thereof. For example, if a fluorescent material is used as a label, luminescence or color change occurs when a target material is present. Therefore, by measuring this, the target material can be detected. For example, it is possible to check whether the target material is detected or not by scanning a well in which a reaction occurs with an image scanner capable of detecting fluorescent pigments, and it is possible to measure a detectable amount by measuring a concentration from the image with software.

The present invention further relates to a solid phase carrier immobilizing a nucleic acid aptamer having a sequence selected from the group consisting of the base sequences set forth in SEQ ID NOS: 19 to 28 in which the nucleic acid aptamer is specifically bound to a Bovine Viral Diarrhea Virus type 1.

A kind of the solid phase carrier and a method for immobilizing the aptamer are the same as described above.

The solid phase carrier of the invention can be used to purify, separate, detect or quantitate the Bovine Viral Diarrhea Virus type 1.

A method for detecting a Bovine Viral Diarrhea Virus type 1 using the solid phase carrier immobilizing the aptamer is the same as described above.

The detection of the Bovine Viral Diarrhea Virus type 1 using the solid phase carrier can be used to diagnose bovine viral diarrhea.

Further, the present invention can be provided in the form of a kit for detecting a Bovine Viral Diarrhea Virus type 1 or a kit for diagnosing bovine viral diarrhea comprising: a nucleic acid aptamer which has any one of base sequences of SEQ ID NOS: 19 to 28 and can be specifically bound to the Bovine Viral Diarrhea Virus type 1.

The kit for detecting a Bovine Viral Diarrhea Virus type 1 or for diagnosing bovine viral diarrhea may be provided in the form of bottles, tubs, sachets, envelopes, tubes, ampoules, etc. which may be partially or entirely made of plastic, glass, paper, foil, wax, etc. Such a container may be equipped with a stopper which may be a part of the container or can be attached to the container mechanically or by means of adhesion or other means and can be entirely or partially detached from the container. Further, the container may be equipped with a stopper which can approach the contents via an injection needle. The kit may include an exterior package, and the exterior package may include an instruction manual about use of the components.

The aptamer specifically bound to the Bovine Viral Diarrhea Virus type 1 according to the present invention specifically detects the Bovine Viral Diarrhea Virus type 1 only. Therefore, it is obvious to one of ordinary skill in the art that a composition for separating the Bovine Viral Diarrhea Virus type 1 comprising the same can be provided.

Therefore, the present invention relates to a composition for separating a Bovine Viral Diarrhea Virus type 1 comprising: a nucleic acid aptamer having a sequence selected from the group consisting of the base sequences set forth in SEQ ID NOS: 19 to 28 in which the nucleic acid aptamer is specifically bound to a Bovine Viral Diarrhea Virus type 1.

Further, the present invention provides a Bovine Viral Diarrhea Virus type 1 separation method comprising: bringing a Bovine Viral Diarrhea Virus type 1-containing sample in contact with a solid phase carrier immobilizing a nucleic acid aptamer having a sequence selected from the group consisting of the base sequences set forth in SEQ ID NOS: 19 to 28 in which the nucleic acid aptamer is specifically bound to a Bovine Viral Diarrhea Virus type 1; and eluting the Bovine Viral Diarrhea Virus type 1 bound to the solid phase carrier using an eluent.

According to an aspect of the present invention, preferably, a column is filled with beads immobilizing the aptamer and a Bovine Viral Diarrhea Virus type 1-containing sample passes through the column, whereby it is possible to separate the Bovine Viral Diarrhea Virus type 1.

Hereinafter, the present invention will be described in detail by means of Examples. However, it should be understood that the following Example are given by way of illustration of the present invention only, and are not intended to limit the scope of the present invention.

Example 1

Selection of Nampt Specific Aptamer

As a DNA pool of 66 mers, a DNA pool including a PCR primer region at both ends and any 30 bases at its center was synthesized.

```
5'-CGTACGGAATTCGCTAGC-N30-GGATCCGAGCTCCACGTG-3'
(SEQ ID NO: 1: CGTACGGAATTCGCTAGC; SEQ ID NO: 2:
GGATCCGAGCTCCACGTG)
```

This DNA pool was put into a buffer solution (pH 7.4, 20 mM Tris, 100 mM NaCl, 2 mM $MgCl_2$) and mixed with Nampt (a Nampt protein produced by AdipoGen Inc., Prod. No. AG-40A-0031) in the same amount and reacted at normal temperature for 30 minutes. Then, in order to remove DNA which was not bound to Nampt, the mixture solution was reacted with a graphene solution for 2 hours. In this case, a single-stranded DNA which was not bound to a target was strongly adsorbed onto a surface of graphene by π-stacking.

The graphene was separated through centrifugation, and a supernatant was taken out to obtain a single-stranded DNA bound to the target by an ethanol precipitation method. An amount of the DNA bound to Nampt obtained as such was measured using a spectrophotometer.

In order to increase the amount of the DNA specifically bound to Nampt, a PCR was carried out using the already-known primer regions. The PCR product is a double-stranded DNA, and thus fluorescein was immobilized to a primer in order to separate the double-stranded DNA into single-stranded DNAs.

```
Forward primer:
                                        (SEQ ID NO: 1)
    5'-fluorescein-CGTACGGAATTCGCTAGC-3'

Reverse primer:
                                        (SEQ ID NO: 3)
    5'-CACGTGGAGCTCGGATCC-3'
```

After the PCR product was purified using a purification kit, polyacrylamide gel electrophoresis was carried out to separate the double-stranded DNA into single-stranded DNAs.

10% polyacrylamide gel contained 6 M urea and 20% formamide, and thus, after the electrophoresis, two bands were formed. During the electrophoresis, the double-stranded DNA was denatured, and a DNA strand with fluorescein and a DNA strand without the fluorescein were positioned up and down, respectively.

The DNA band with fluorescein was cut off and extracted from the polyacrylamide gel, and then the separated DNA was obtained by performing the ethanol precipitation method again. The DNA pool obtained as such was reacted with Nampt again. A schematic diagram of such a process is shown in FIG. 1. A selection process including a series of processes was carried out five times in total to develop an aptamer. After the fourth selection process, a counter selection process was carried out with HSA and other adipokines such as adiponectin, RBP4 (Retinol Binding Protein 4), resistin, and vaspin to block a DNA which was not specifically bound and obtain a DNA pool which was specifically bound to Nampt only with high affinity. In the counter selection process, unlike a general process, instead of Nampt, the above-described counter targets were reacted with the DNA pool in the same buffer for 30 minutes and then reacted with a graphene solution for 2 hours. In this process, a single-stranded DNA which was not bound to a counter target was adsorbed onto a surface of graphene. A supernatant was removed by centrifugation and only graphene was taken out to obtain a single-stranded DNA adsorbed onto the graphene from the graphene. To do so, the Nampt was reacted on the surface of the graphene onto which the single-stranded DNA was adsorbed, and the Nampt as a main target caused a conformational change of the single-stranded DNA adsorbed onto the graphene to effectively separate the single-stranded DNA from the surface of the graphene. The single-stranded DNA separated as such became a candidate for an aptamer which was not bound to the counter target but strongly bound to the Nampt as a main target.

Figure 2:
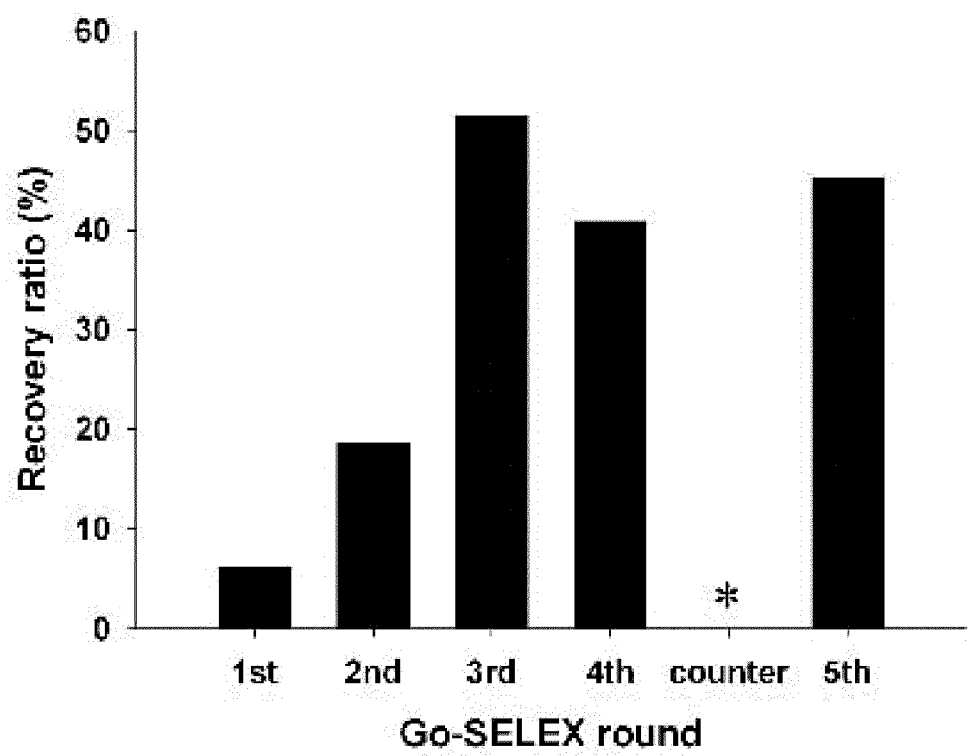
FIG. 2 illustrates an increasing ratio of single-stranded DNA bound to a Nampt protein as a target model in a graphene oxide-based aptamer development process according to the present invention.
Figure 3:
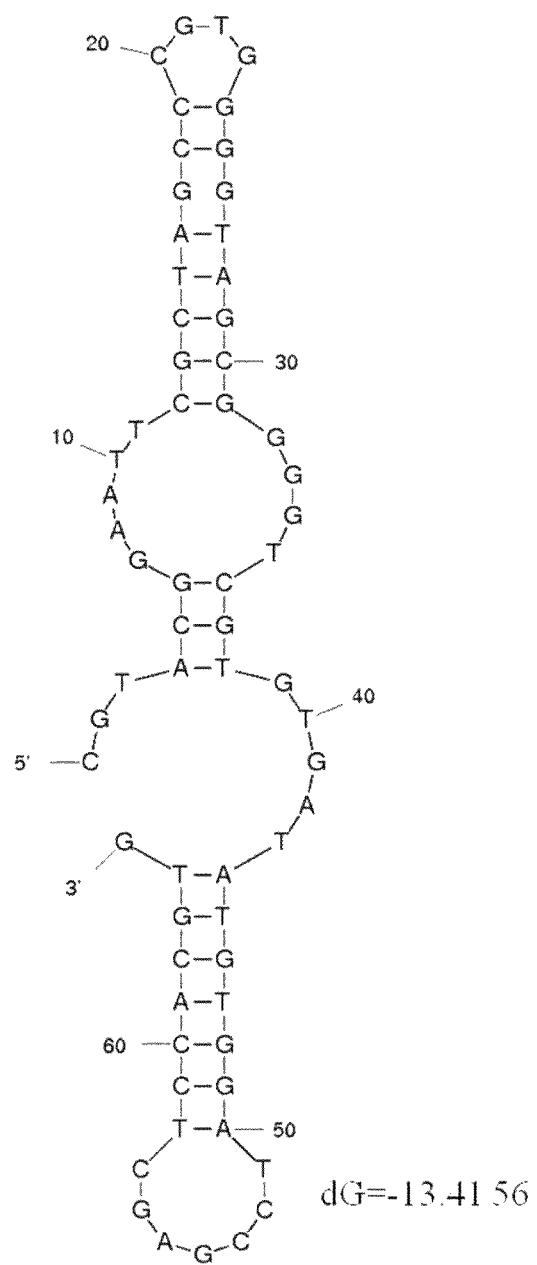
FIGS. 3 to 17 provide schematic diagrams of secondary structures of DNA aptamers obtained by analyzing base sequences of 15 nucleic acid aptamers bound to a Nampt protein with the web server-based M-fold program according to the present invention.
Figure 4:
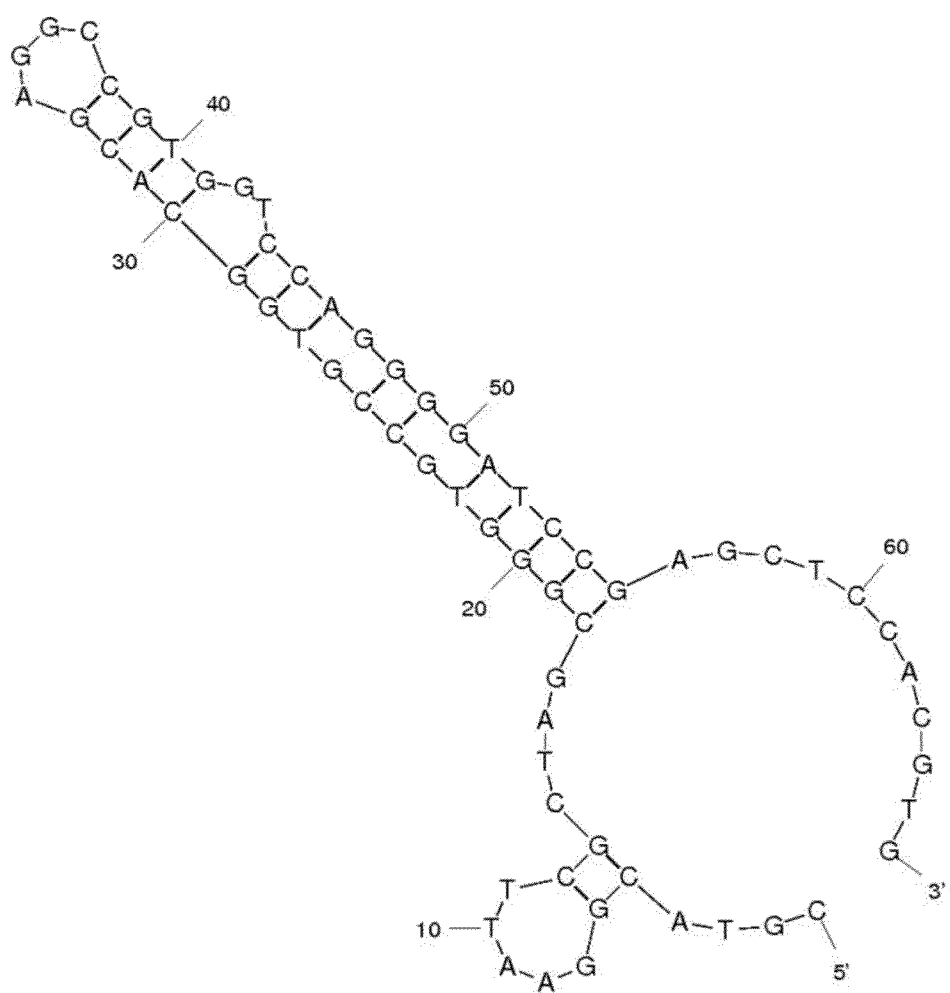
Figure 5:
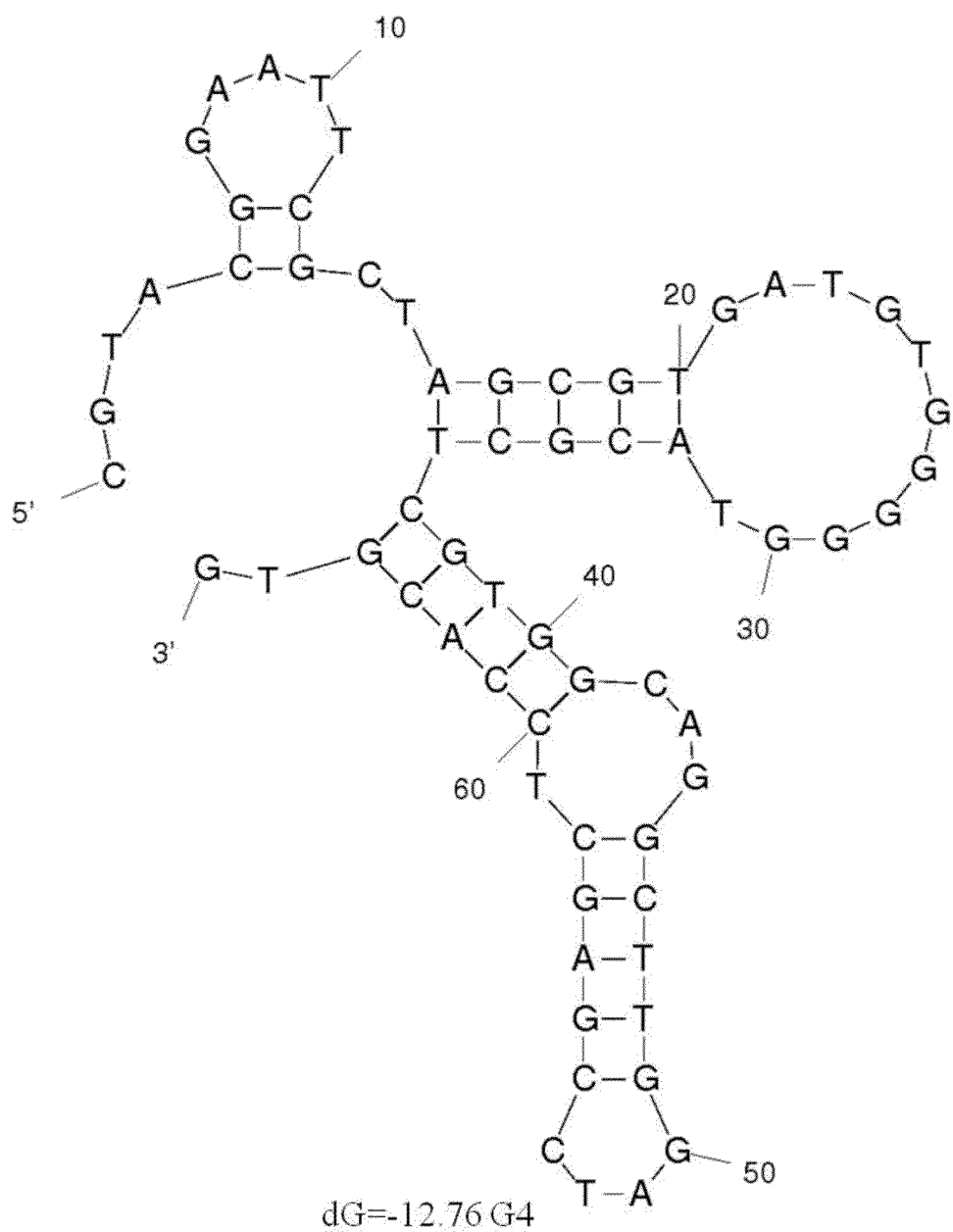
Figure 6:
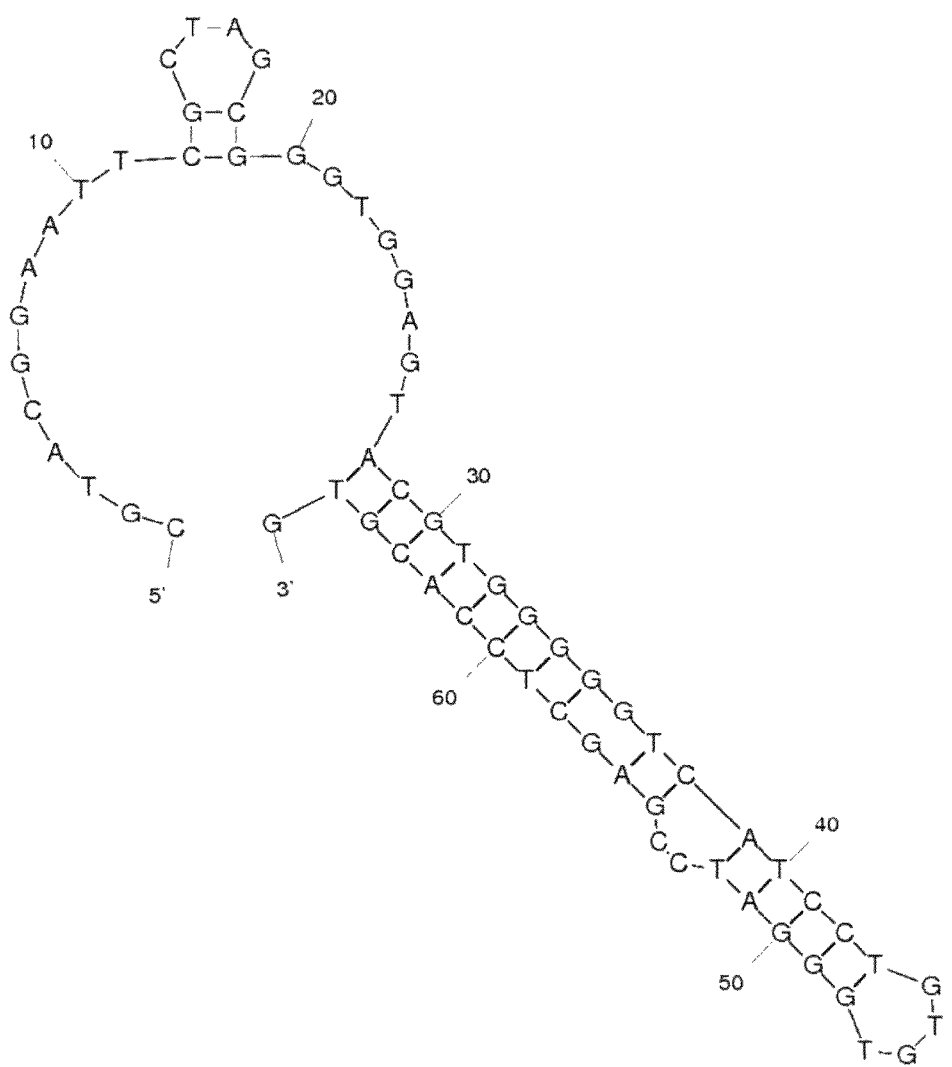
Figure 7:
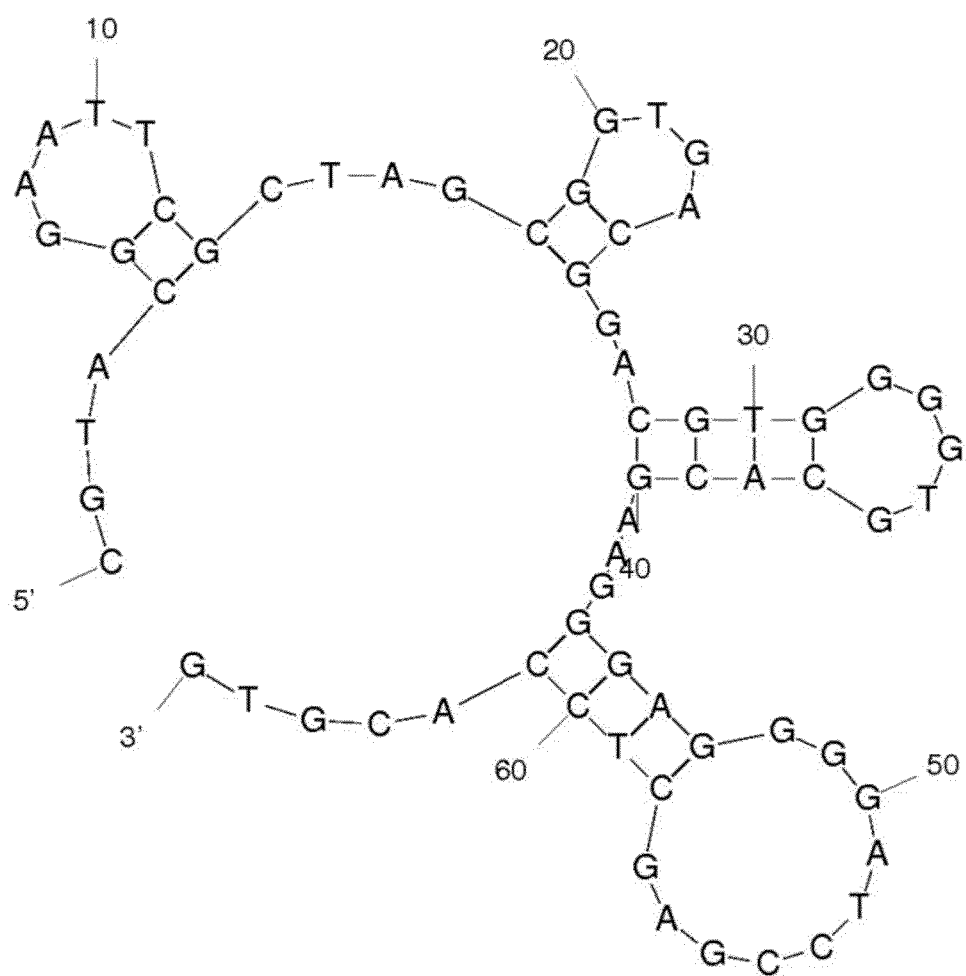
Figure 8:
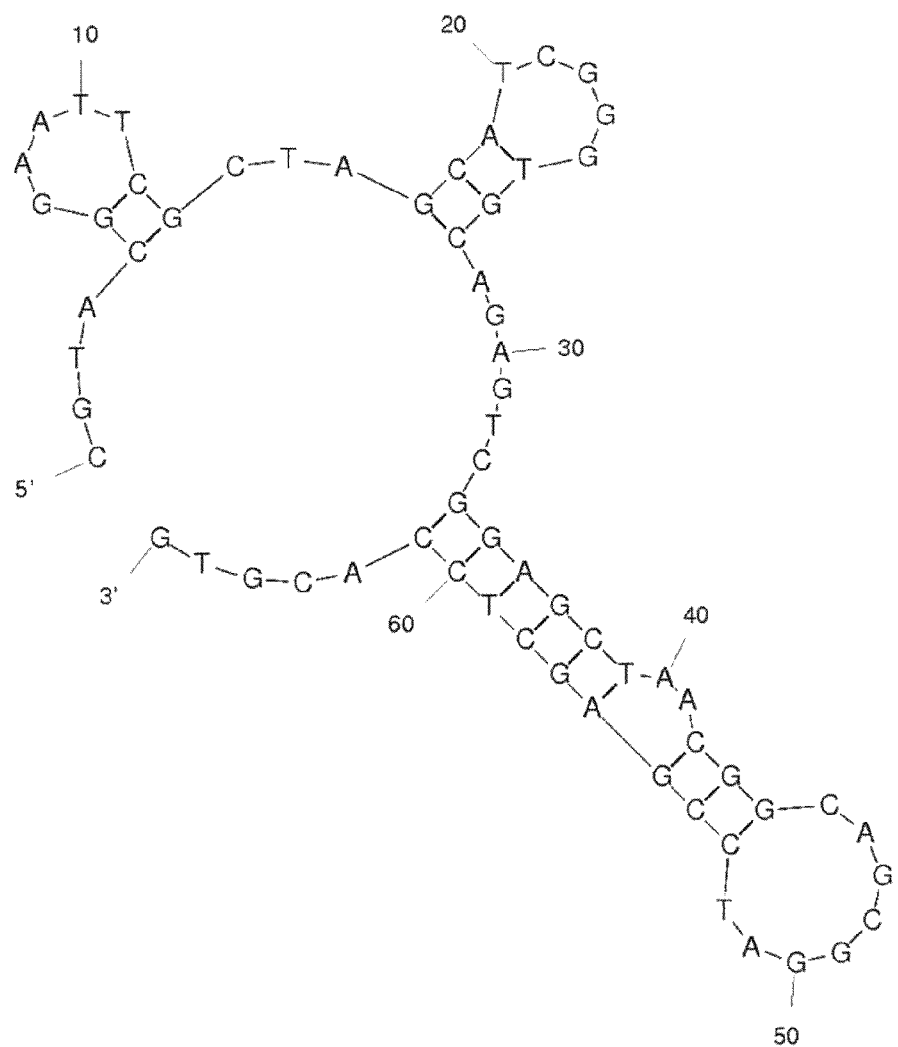
Figure 9:
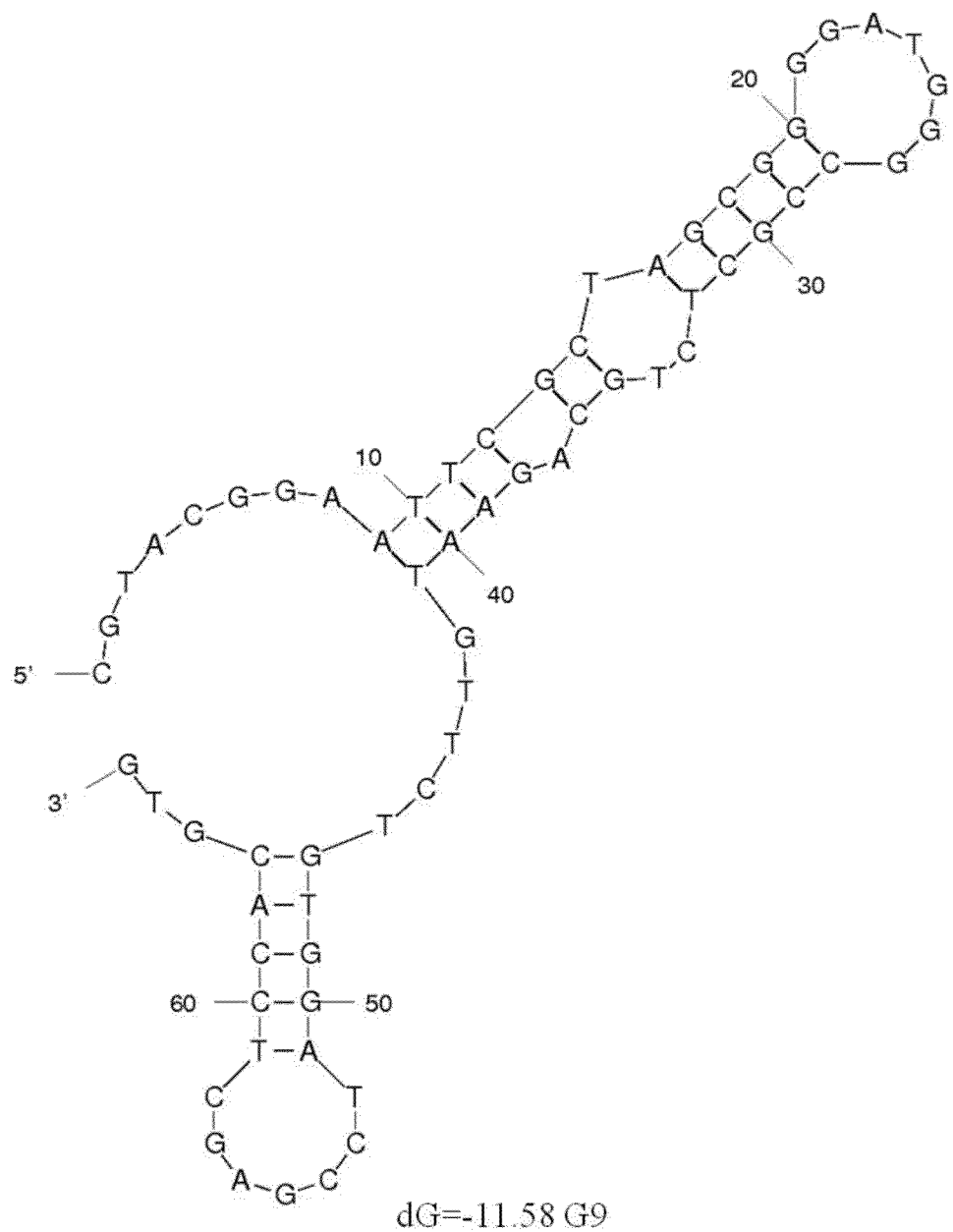
Figure 10:
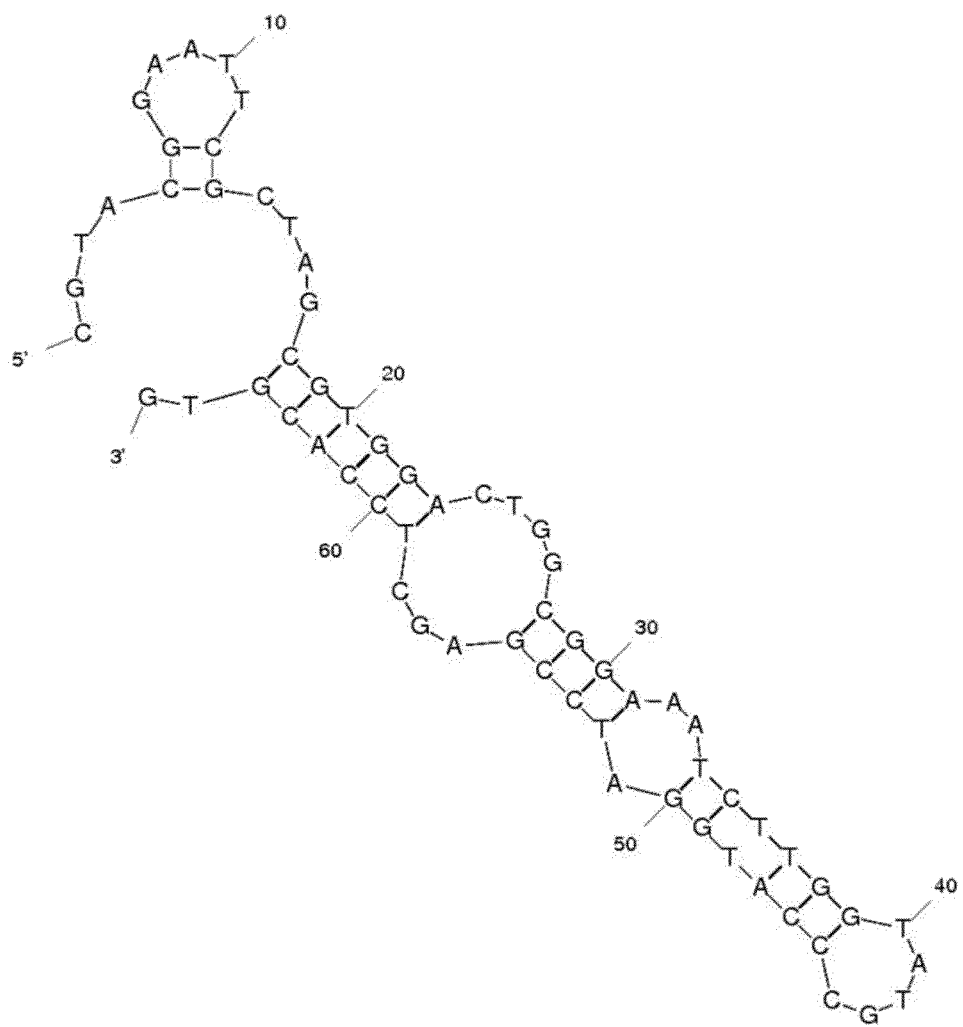
Figure 11:
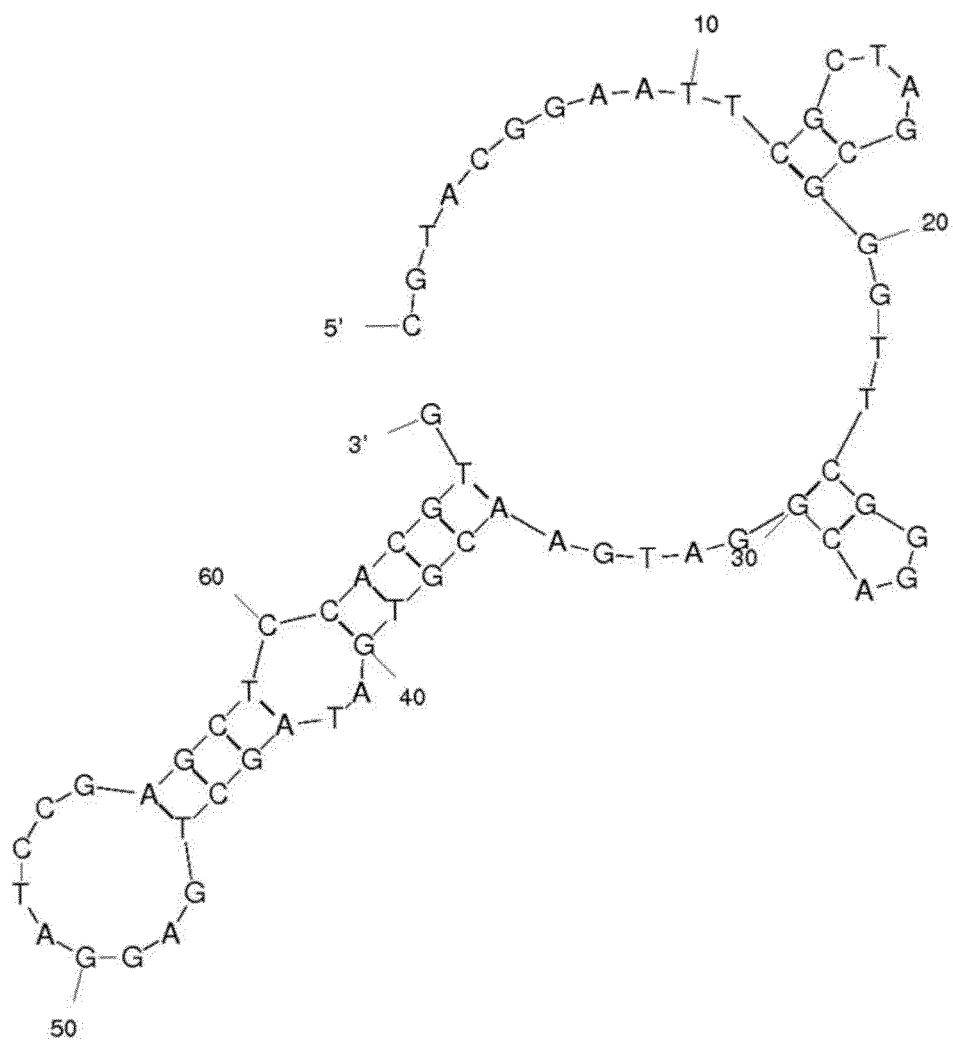
Figure 12:
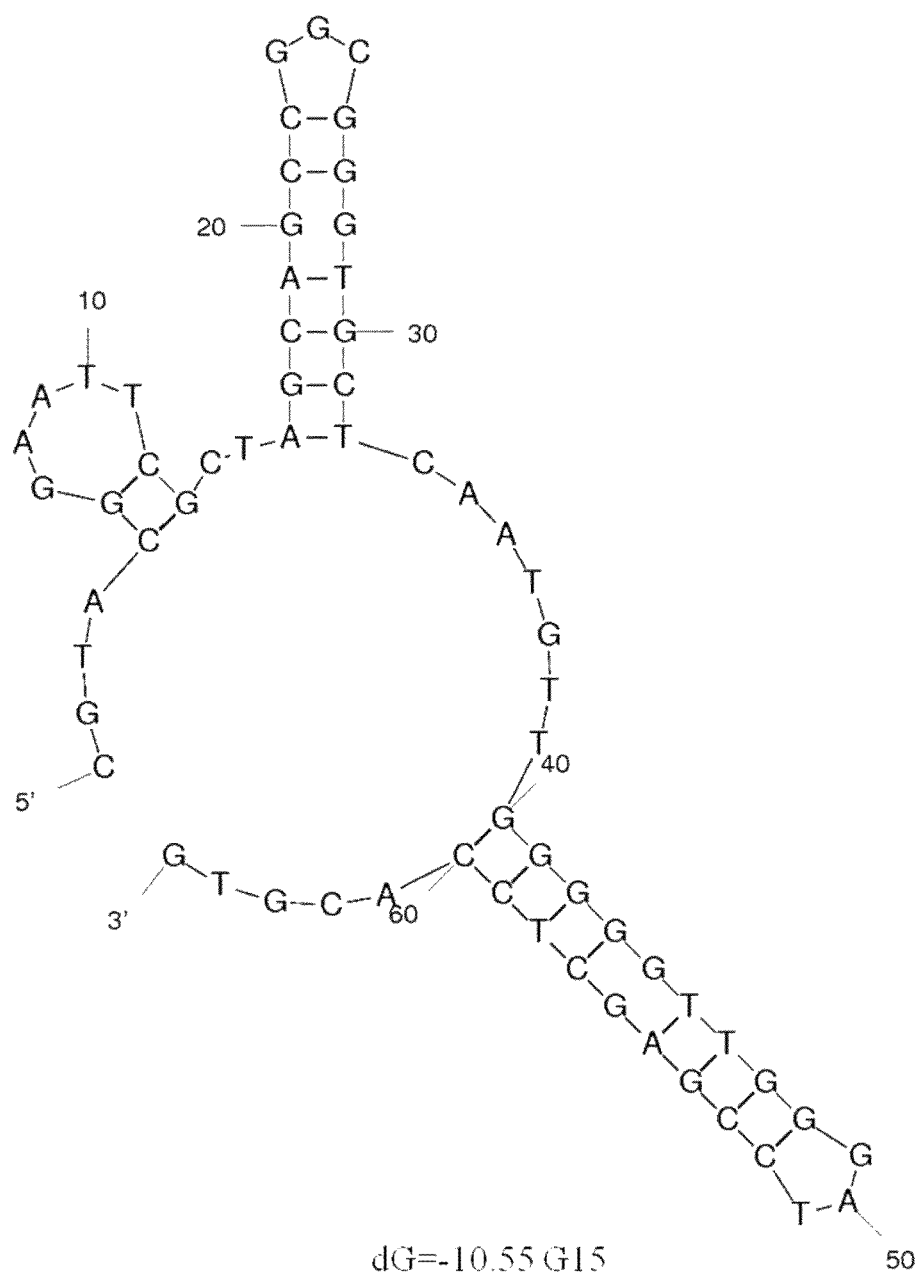
Figure 13:
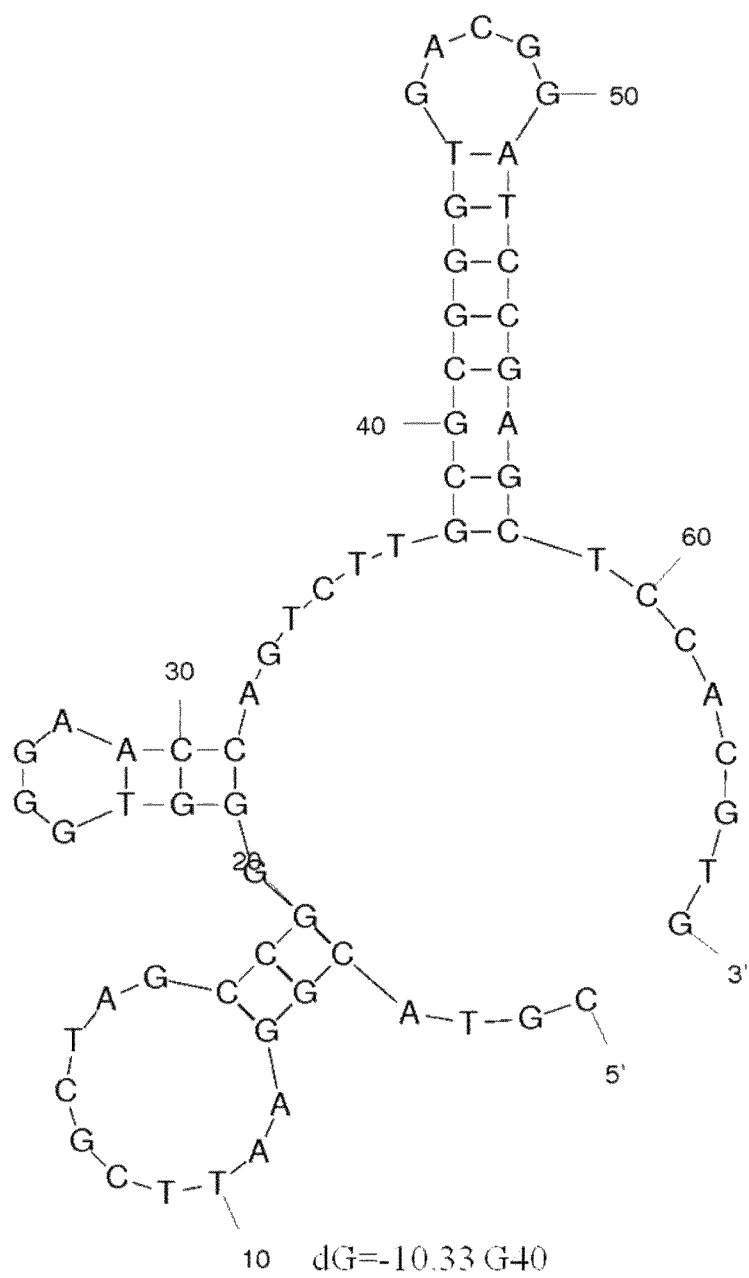
Figure 14:
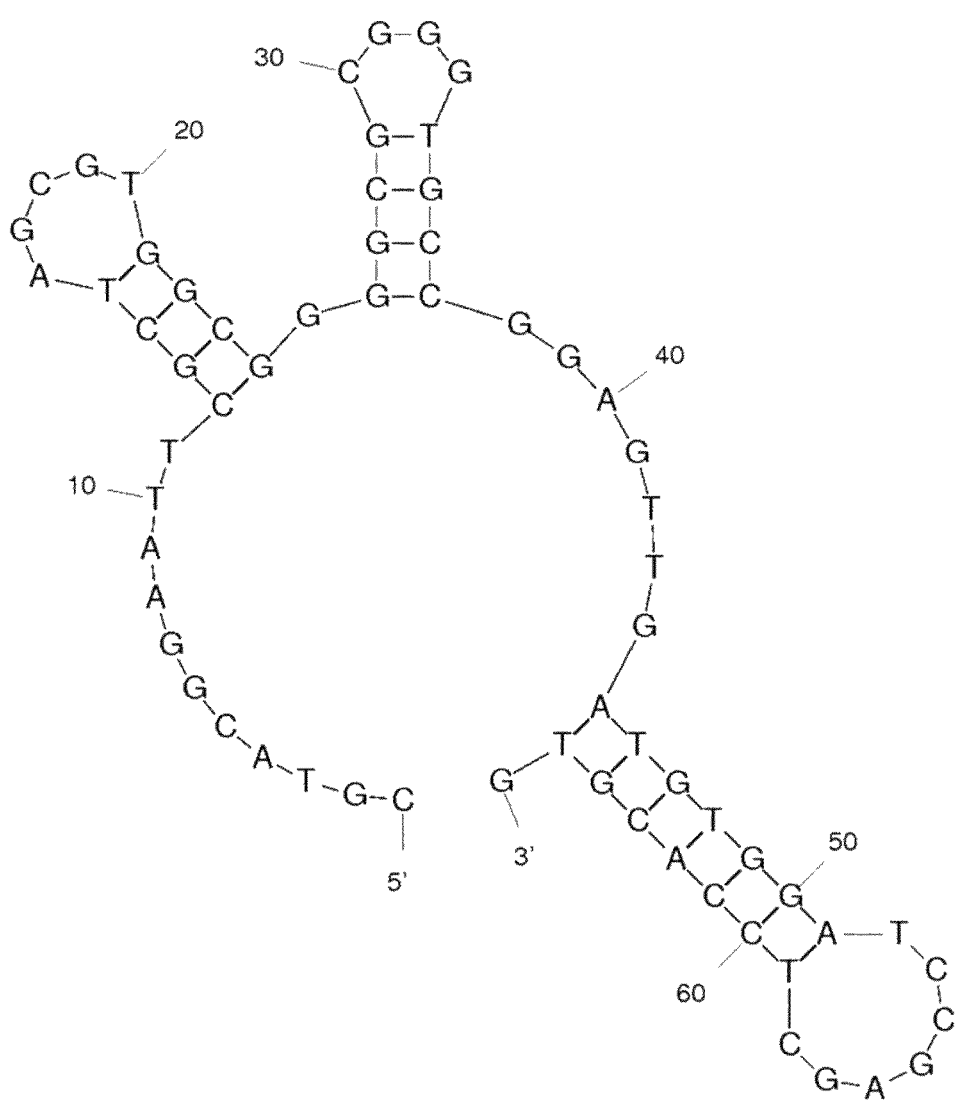
Figure 15:
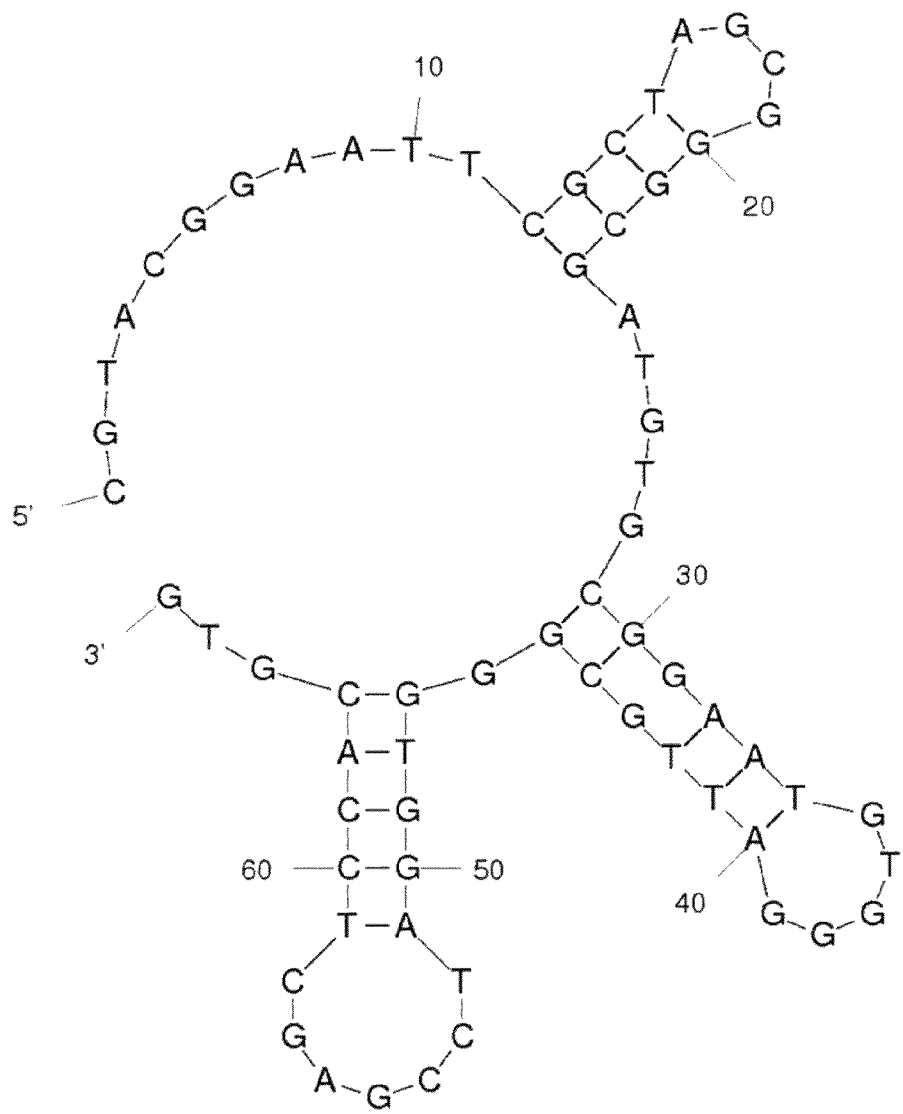
Figure 16:
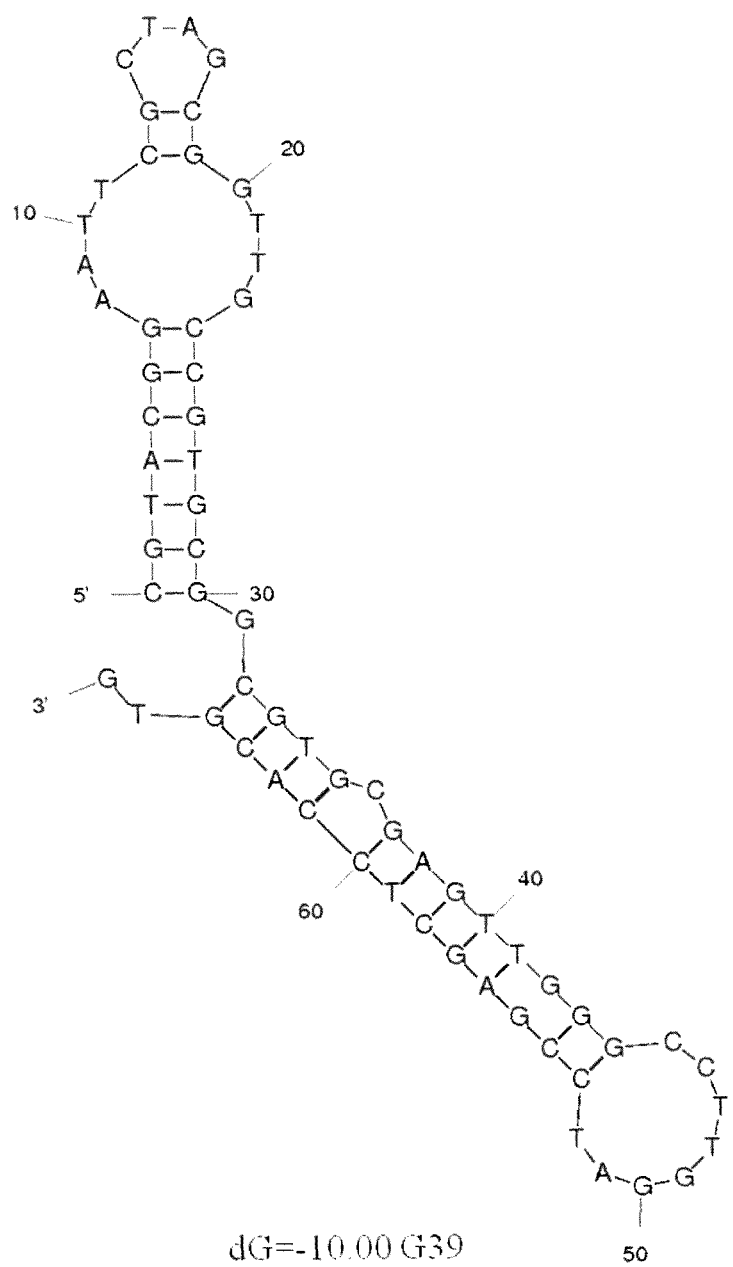
Figure 17:
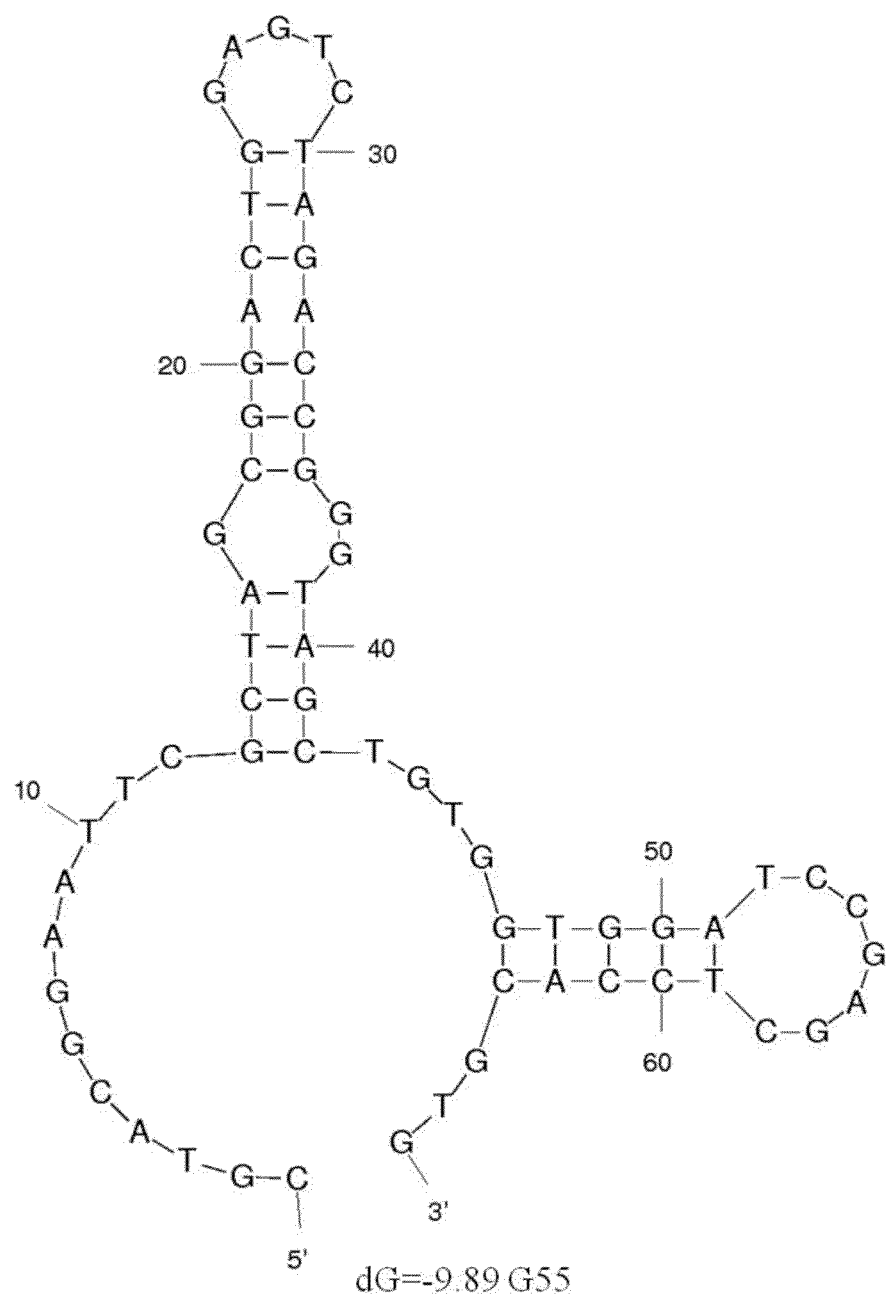

FIG. 2 illustrates a percentage of single-stranded DNA bound to Nampt in each selection round.

The DNA pool finally obtained was cloned using a pDrive Cloning Vector, and DNA was extracted from a resultant colony to carry out a base sequence analysis. As a result, 15 kinds of DNAs specifically bound to Nampt were obtained.

A result of analysis on base sequences of the 15 kinds of DNAs specifically bound to Nampt with high affinity is shown in Table 1. Further, a result of prediction about secondary structures of these 15 kinds of aptamers using the M-fold program is shown in FIGS. 3 to 17.

TABLE 1

| SEQ ID NOS | Aptamer No. | Sequence (5'-3') |
|---|---|---|
| 4 | G56 | CGTACGGAATTCGCTAGCCCGTGGGGTAGCGGGGTCGTGTGATATGTGGATCCGAGCTCCACGTG |
| 5 | G12 | CGTACGGAATTCGCTAGCGGGTGCCGTGGCACGAGGCCGTGGTCCAGGGGATCCGAGCTCCACGTG |
| 6 | G4 | CGTACGGAATTCGCTAGCGTGATGTGGGGGTACGCTCGTGGCAGGCTTGGATCCGAGCTCCACGTG |
| 7 | G27 | CGTACGGAATTCGCTAGCGGGTGGAGTACGTGGGGGTCATCCTGTGTGGGATCCGAGCTCCACGTG |
| 8 | G35 | CGTACGGAATTCGCTAGCGGTGACGGACGTGGGGTGCACGAAGGGAGGGGATCCGAGCTCCACGTG |

TABLE 1 -continued

| SEQ ID NOS | Aptamer No. | Sequence (5'-3') |
|---|---|---|
| 9 | G26 | CGTACGGAATTCGCTAGCATCGGGTGCAGAGTCGGAGCTAACGGCAGCGGATCCGAGCTCCACGTG |
| 10 | G9 | CGTACGGAATTCGCTAGCGGGGATGGGCCGCTCTGCAGAATGTTCTGTGGATCCGAGCTCCACGTG |
| 11 | G32 | CGTACGGAATTCGCTAGCGTGGACTGGCGGAAATCTTGGTATGCCCATGGATCCGAGCTCCACGTG |
| 12 | G21 | CGTACGGAATTCGCTAGCGGGTTCGGGACGGATGAACGTGATAGCTGAGGATCCGAGCTCCACGTG |
| 13 | G15 | CGTACGGAATTCGCTAGCAGCCGGCGGGTGCTCAATGTTGGGGGTTGGGATCCGAGCTCCACGTG |
| 14 | G40 | CGTACGGAATTCGCTAGCCGGGGTGGGAACCAGTCTTGCGCGGGTGACGGATCCGAGCTCCACGTG |
| 15 | G54 | CGTACGGAATTCGCTAGCGTGGCGGGGCGCGGGTGCCGGAGTTGATGTGGATCCGAGCTCCACGTG |
| 16 | G37 | CGTACGGAATTCGCTAGCGGGCGATGTGCGGAATGTGGGATTGCGGGTGGATCCGAGCTCCACGTG |
| 17 | G39 | CGTACGGAATTCGCTAGCGGTTGCCGTGCGGCGTGCGAGTTGGGCCTTGGATCCGAGCTCCACGTG |
| 18 | G55 | CGTACGGAATTCGCTAGCGGACTGGAGTCTAGACCGGGTAGCTGTGGTGGATCCGAGCTCCACGTG |

Example 2

Analysis on Nampt Binding Specificity

An experiment showing that 15 kinds of aptamers strongly bound to Nampt were not bound to other blood proteins but specifically bound to Nampt only was carried out by immobilizing aptamers onto a gold chip with a surface magnetic resonance device (SPR). Since Nampt was one of adipokines, as the most suitable controls to show that a Nampt aptamer was specifically bound to Nampt only, other adipokines (RBP4, adiponectin, resistin, and vaspin) and HSA were used.

Firstly, a carboxyl group (—COOH) was formed on a surface of a gold chip with 50 mM of 3,3'-dithiodipropionic acid, and a self-assembly monolayer was formed with EDC/NHS. Then, streptavidin was immobilized thereon, and each aptamer bound to biotin was immobilized. Herein, 200 nM Nampt and the controls, i.e., RBP4, adiponectin, resistin, vaspin, and HAS, were reacted for 30 minutes in respective buffer solutions (100 mM NaCl, 2 mM $MgCl_2$, 5 mM KCl, 1 mM $CaCl_2$, and 20 mM Tris-Cl buffer solution containing 0.02% Tween 20, pH 7.6), and non-bound proteins were washed off with the same buffer solutions.

Figure 18:
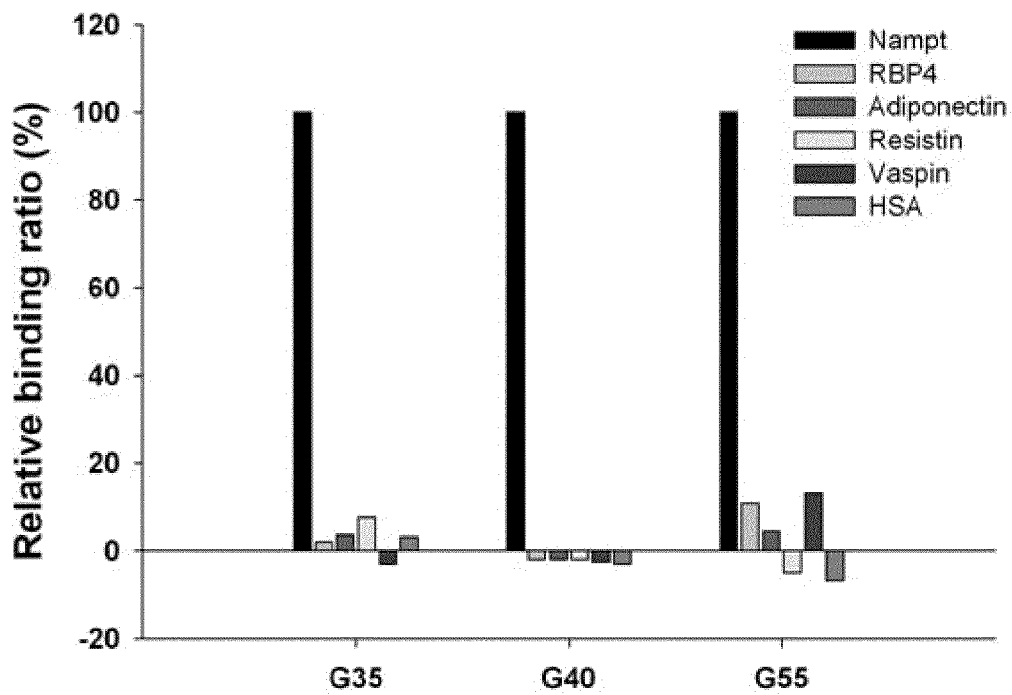
FIG. 18 illustrates a result of analyzing specificity of G35, G40, and G55 aptamers (SEQ ID NOS: 8, 14, and 18) as DNA aptamers bound to a Nampt protein to other adipokines and HAS according to the present invention.

Finally, a result of the SPR was analyzed, and it could be confirmed that the Nampt aptamers were superiorly bound to Nampt compared to other proteins. This result is shown in FIG. 18.

Example 3

Measurement of Dissociation Constant ($K_d$) of Nampt

Aptamers G35, G40, and G55 had the highest specificity and binding force among the 15 kinds of aptamers specifically bound to Nampt and produced in Example 1. Binding of these aptamers with respect to Nampt was analyzed. The aptamers were immobilized onto a gold chip in the same manner as described above, and Nampt at various concentrations of 20 nM to 400 nM was reacted for 30 minutes in buffer solutions (100 mM NaCl, 2 mM $MgCl_2$, 5 mM KCl, 1 mM $CaCl_2$, and 20 mM Tris-Cl buffer solution containing 0.02% Tween 20, pH 7.6). In order to obtain a dissociation constant, each reaction level was plotted by a nonlinear regression method and a single site saturation ligand binding method with Graphpad Prism 5.0. In this case, the equation $Y=B_{max}*X^h/(K_d^h+X^h)$ was used (y represents a saturation degree, $B_{max}$ represents a maximal binding site, $K_d$ represents a dissociation constant, X represents non-bound Nampt, and h represents a hill slope constant).

Figure 19:
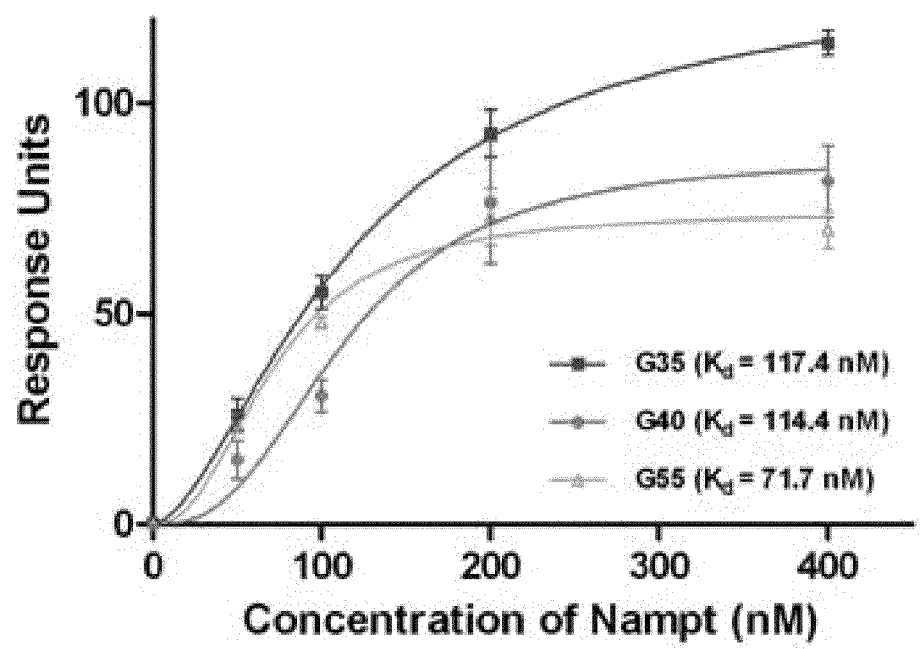
FIG. 19 illustrates a result of analyzing binding force of G35, G40, and G55 aptamers (SEQ ID NOS: 8, 14, and 18) having a high binding specificity to a Nampt protein, according to the present invention.

As a result, the $K_d$ values of the aptamers G35, G40, and G55 were 117.4 nM, 114.4 nM, and 71.7 nM, respectively, and thus it was confirmed that they were strongly bound to Nampt. Analysis data thereof is shown in FIG. 19.

Example 4

Selection of Bovine Viral Diarrhea Virus Type 1 Specific Aptamer

As a DNA pool of 66 mers, a DNA pool including a PCR primer region at both ends and any 30 bases at its center was synthesized.

```
5'-CGTACGGAATTCGCTAGC-N30-GGATCCGAGCTCCACGTG-3'
(SEQ ID NO: 1: CGTACGGAATTCGCTAGC; SEQ ID NO: 2:
GGATCCGAGCTCCACGTG) (N: A, T, G, or C)
```

Firstly, the DNA pool was put into a buffer solution (pH 7.4, 20 mM Tris, 100 mM NaCl, 2 mM $MgCl_2$) and mixed with similar substances of a Bovine Viral Diarrhea Virus type 1 as a target material, i.e., BVDV type 2, CSFV (Classical Swine Fever Virus), MDBK (Mardin-Darby Bovine Kidney cell), or BSA (Bovine Serum Albumin), and reacted at normal temperature for 30 minutes. Then, in order to remove DNA which was bound to the similar substances and obtain only DNA which was not bound to the similar substances, the mixture solution was reacted with a graphene solution for 2 hours. In this case, a single-stranded DNA which was not bound to the similar substances was strongly adsorbed onto a surface of graphene by π-stacking. The DNA which was not bound to the similar substances but adsorbed onto the graphene became a candidate for a BVDV type 1 aptamer.

The graphene was separated through centrifugation, a supernatant was discarded, and the separated graphene was washed off three times with the same buffer solution. The BVDV type 1 was put into the washed graphene as a target material and reacted therewith for 2 hours. In this case, the target material was reacted with the DNA adsorbed onto the surface of the graphene and caused a conformational change of DNA, and the conformationally changed DNA was separated from the graphene.

Then, a single-stranded DNA bound to the target was obtained from the DNA separated from the graphene by an ethanol precipitation method. An amount of the DNA bound to the BVDV type 1 obtained as such was measured using a spectrophotometer.

In order to amplify the DNA specifically bound to the BVDV type 1, a PCR was carried out using the already-known primer regions. The PCR product is a double-stranded DNA, and thus fluorescein was immobilized to a primer in order to separate the double-stranded DNA into single-stranded DNAs.

```
Forward primer:
                                        (SEQ ID NO: 1)
5'FP-fluorescein-CGTACGGAATTCGCTAGC-3'

Reverse primer:
                                        (SEQ ID NO: 3)
5'RP-CACGTGGAGCTCGGATCC-3'
```

After the PCR product was purified using a purification kit, polyacrylamide gel electrophoresis was carried out to separate the double-stranded DNA into single-stranded DNAs. 10% polyacrylamide gel contained 6 M urea and 20% formamide, and thus, after the electrophoresis, two bands were formed. During the electrophoresis, the double-stranded DNA was denatured, and a DNA strand with fluorescein and a DNA strand without the fluorescein were positioned up and down, respectively.

The DNA band with fluorescein was cut off to carry out gel extraction, and then the separated DNA was obtained by performing the ethanol precipitation method again. The DNA pool obtained as such was reacted with the similar substances of the BVDV type 1 again. Such a series of processes was repeated. A selection process was carried out five times in total to develop an aptamer. Since DNA which could be bound to the similar substances was removed in each selection process, the aptamer had high selectivity. Further, since DNA was taken out by a conformational change caused by the target material in each process, it was possible to obtain the aptamer having high affinity.

Figure 20:
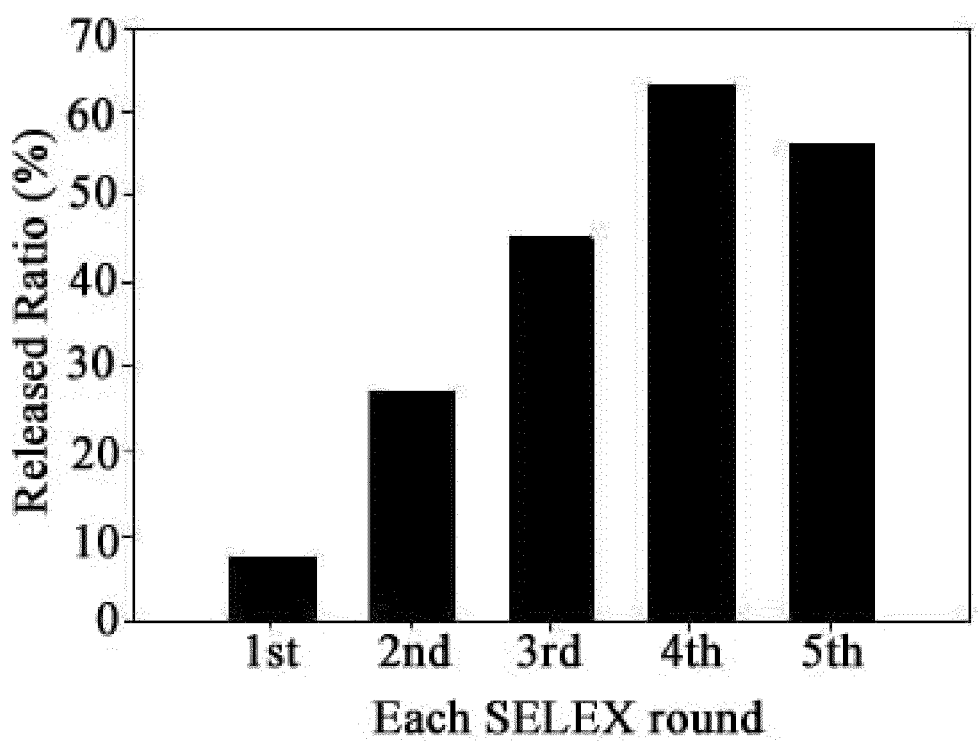
FIG. 20 is a graph showing a percentage of single-stranded DNA bound to a Bovine Viral Diarrhea Virus type 1 (BVDV type 1) as a target material in each selection round in a selection process for separating an aptamer specific to the BVDV type 1.
Figure 21:
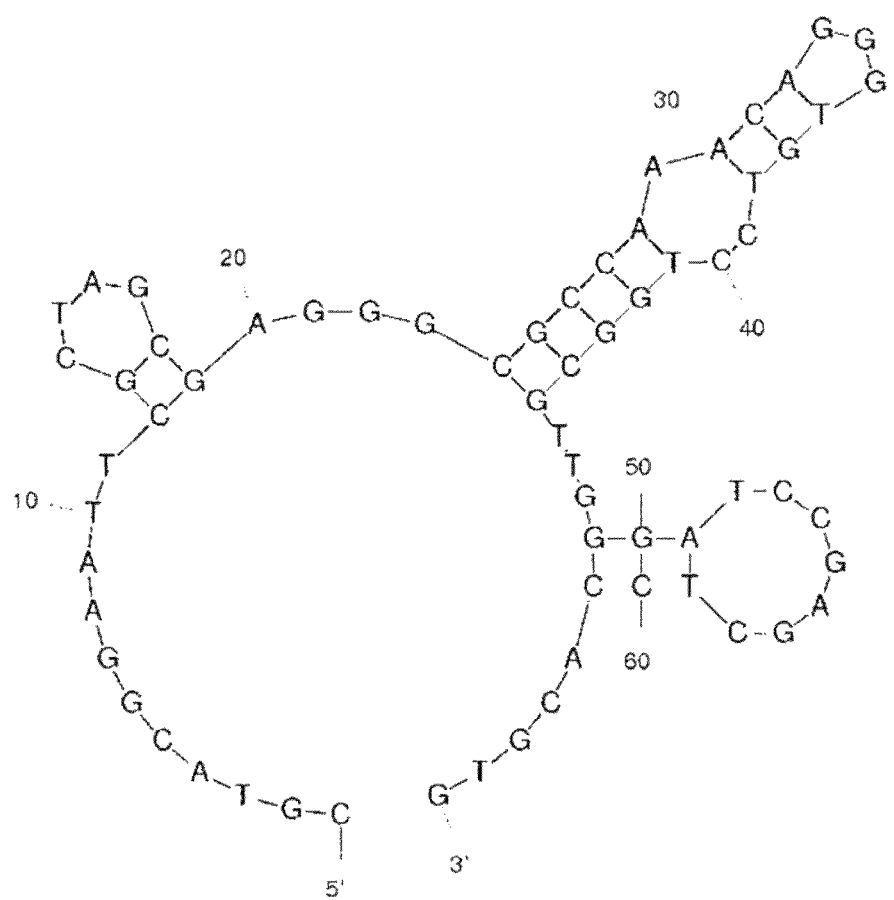
FIGS. 21 to 30 provide schematic diagrams of secondary structures of aptamers obtained by analyzing base sequences of 10 nucleic acid aptamers specific to a BVDV type 1 with the web server-based M-fold program according to the present invention.
Figure 22:
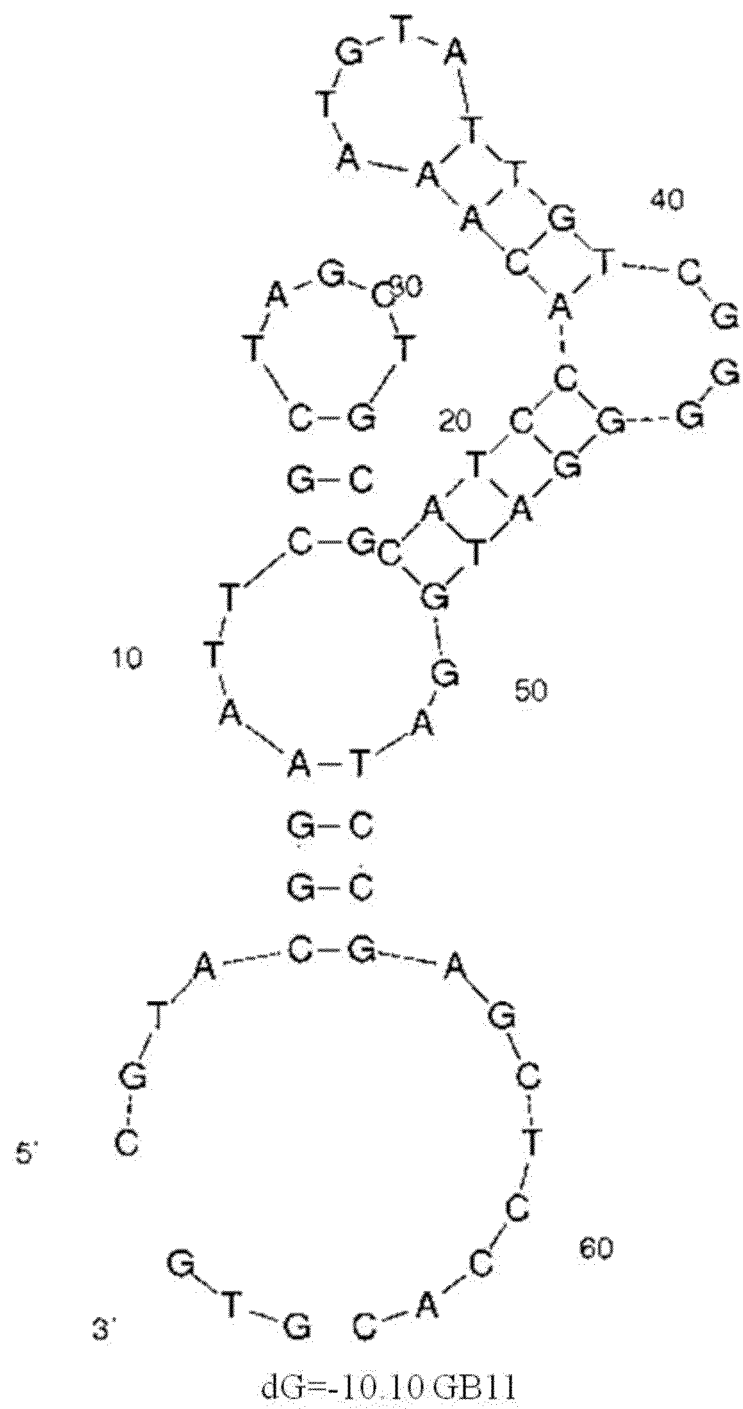
Figure 23:
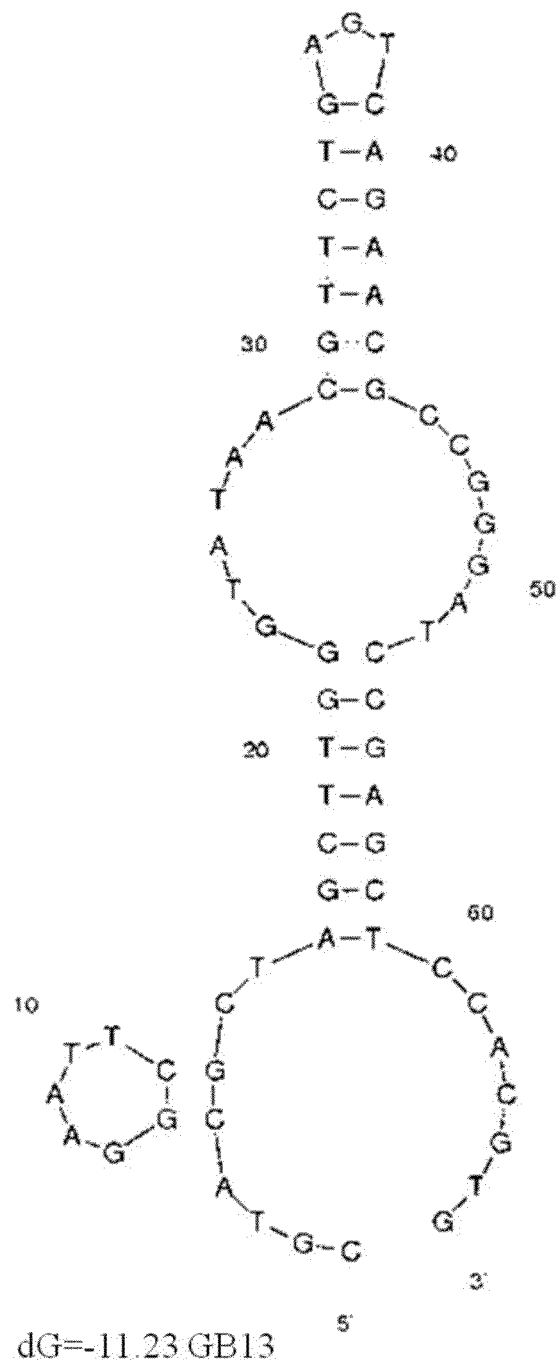
Figure 24:
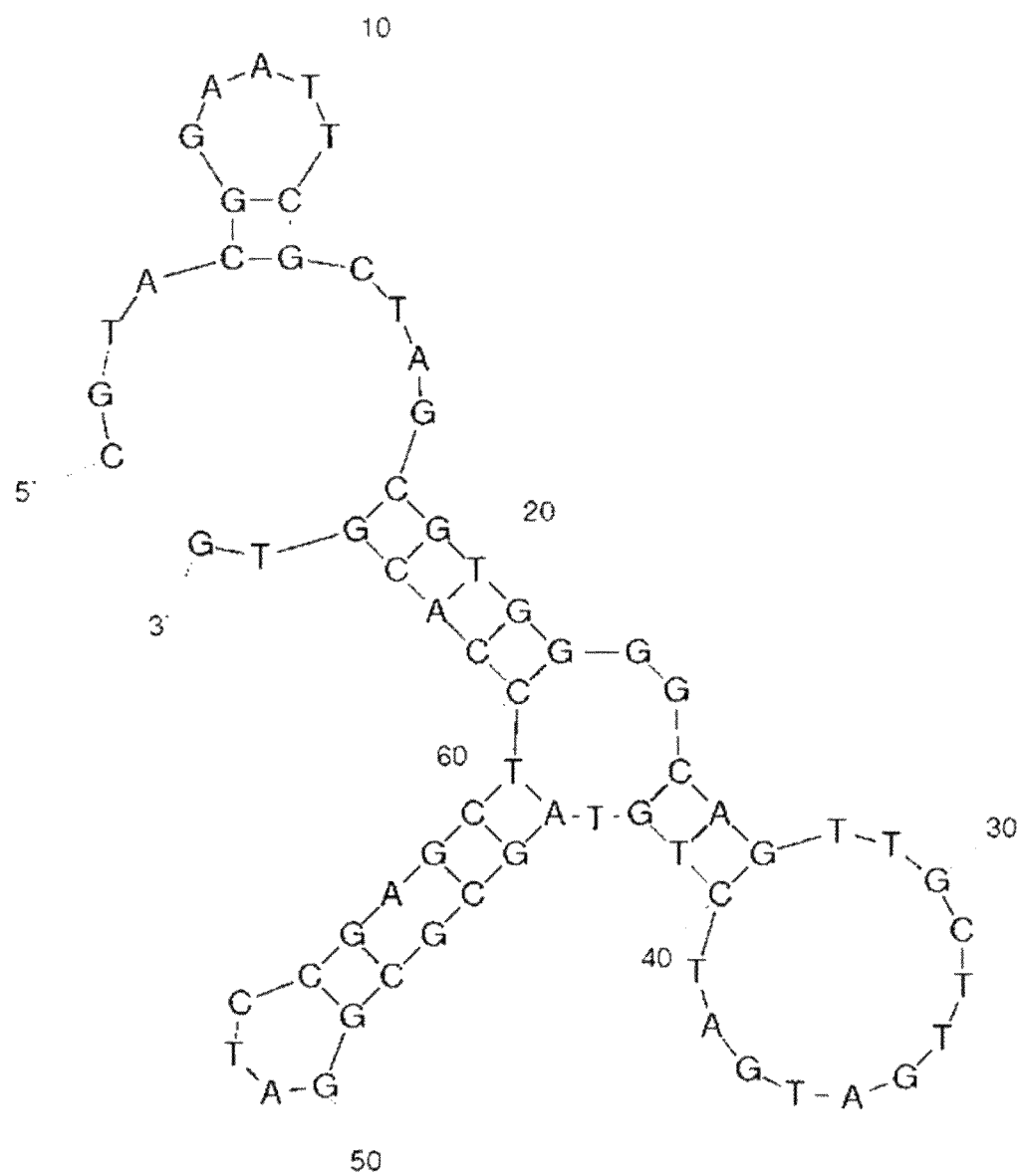
Figure 25:
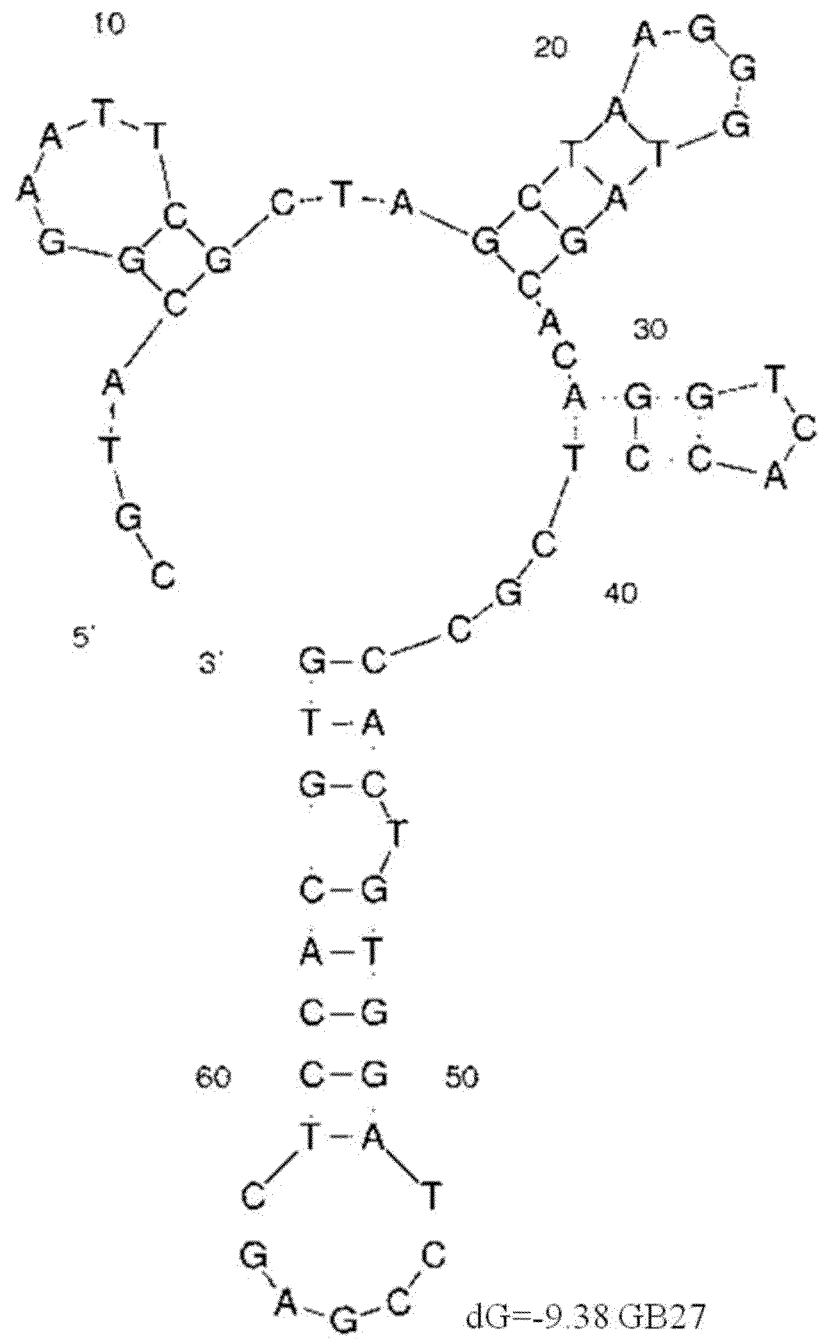
Figure 26:
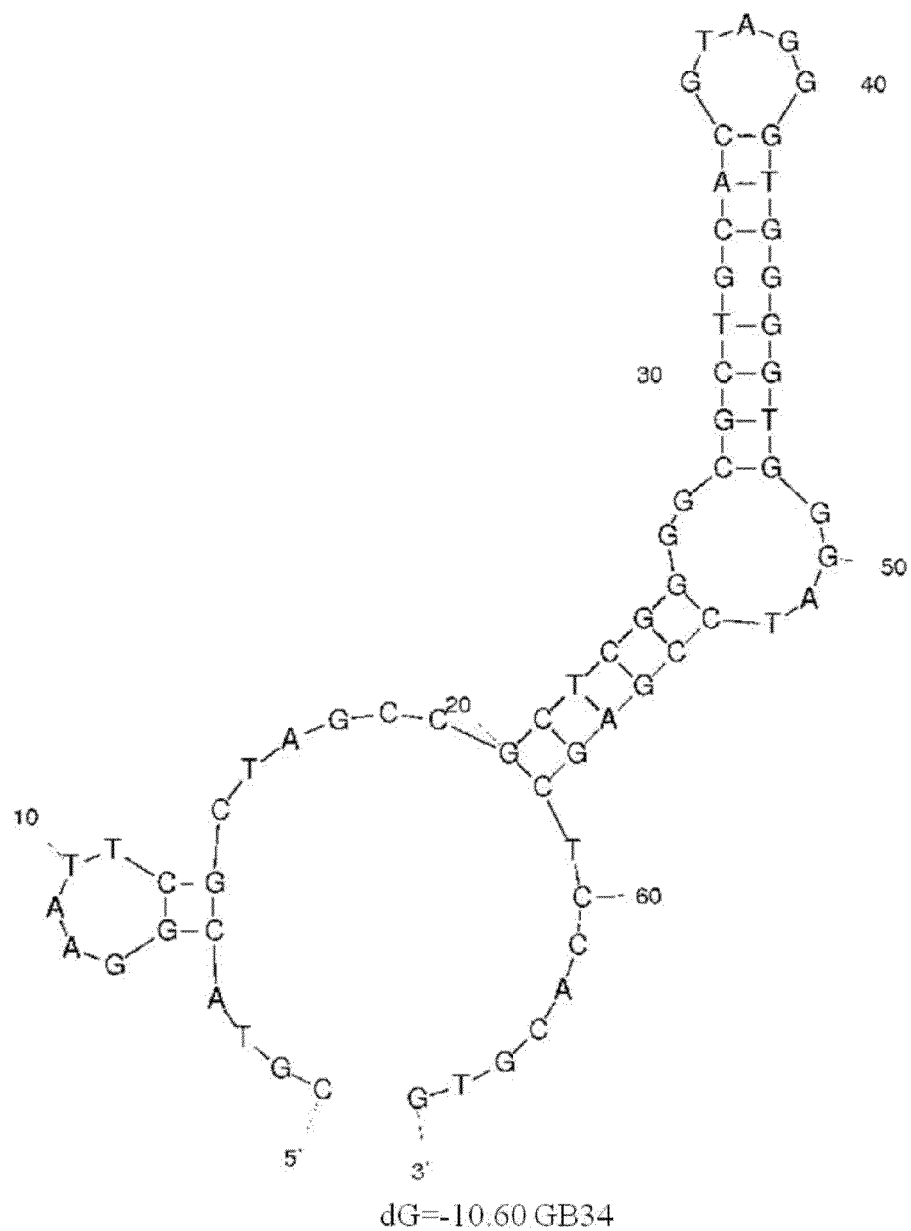
Figure 27:
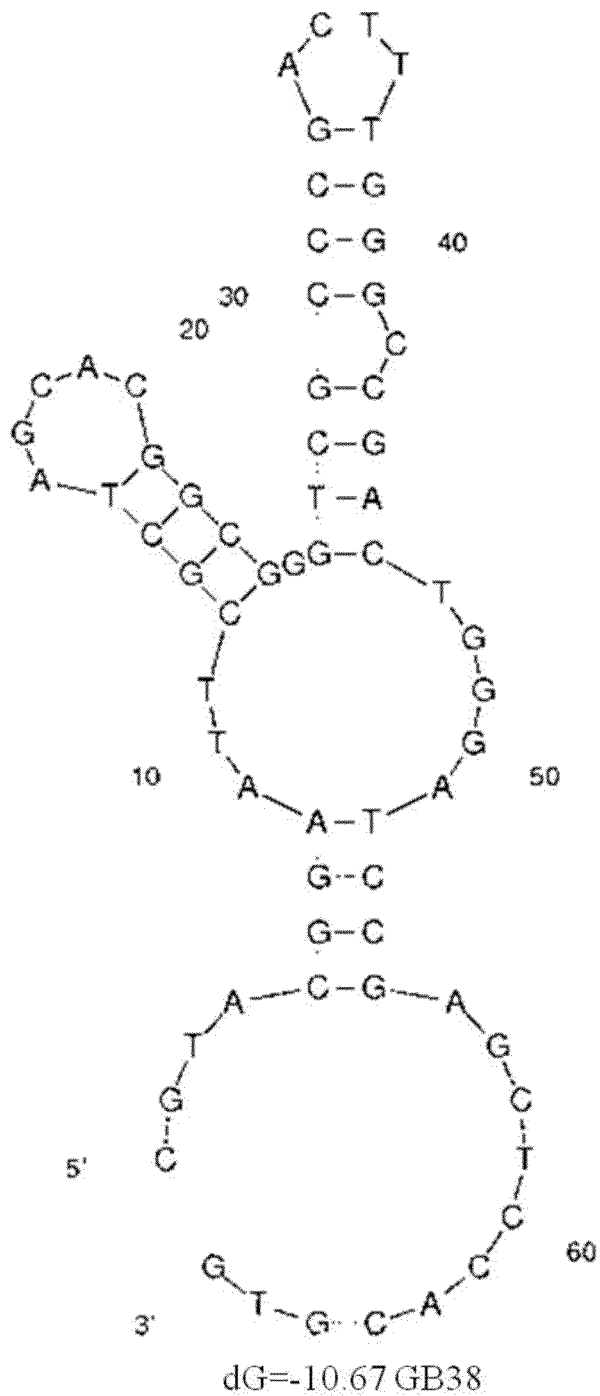
Figure 28:
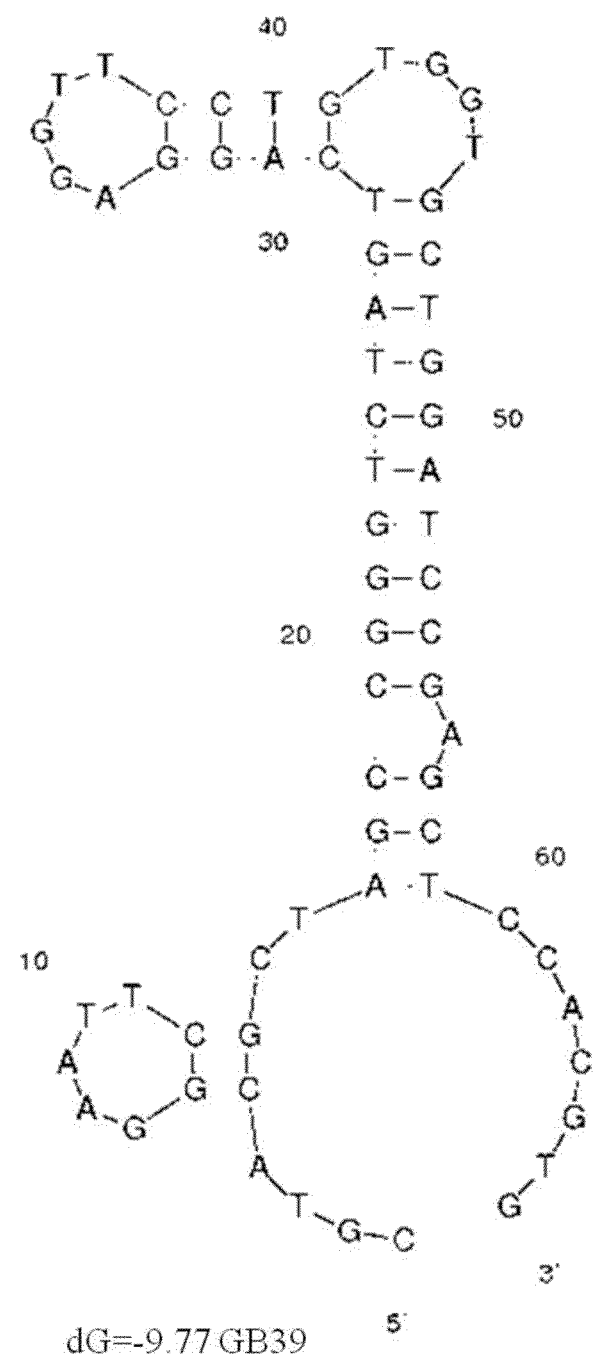
Figure 29:
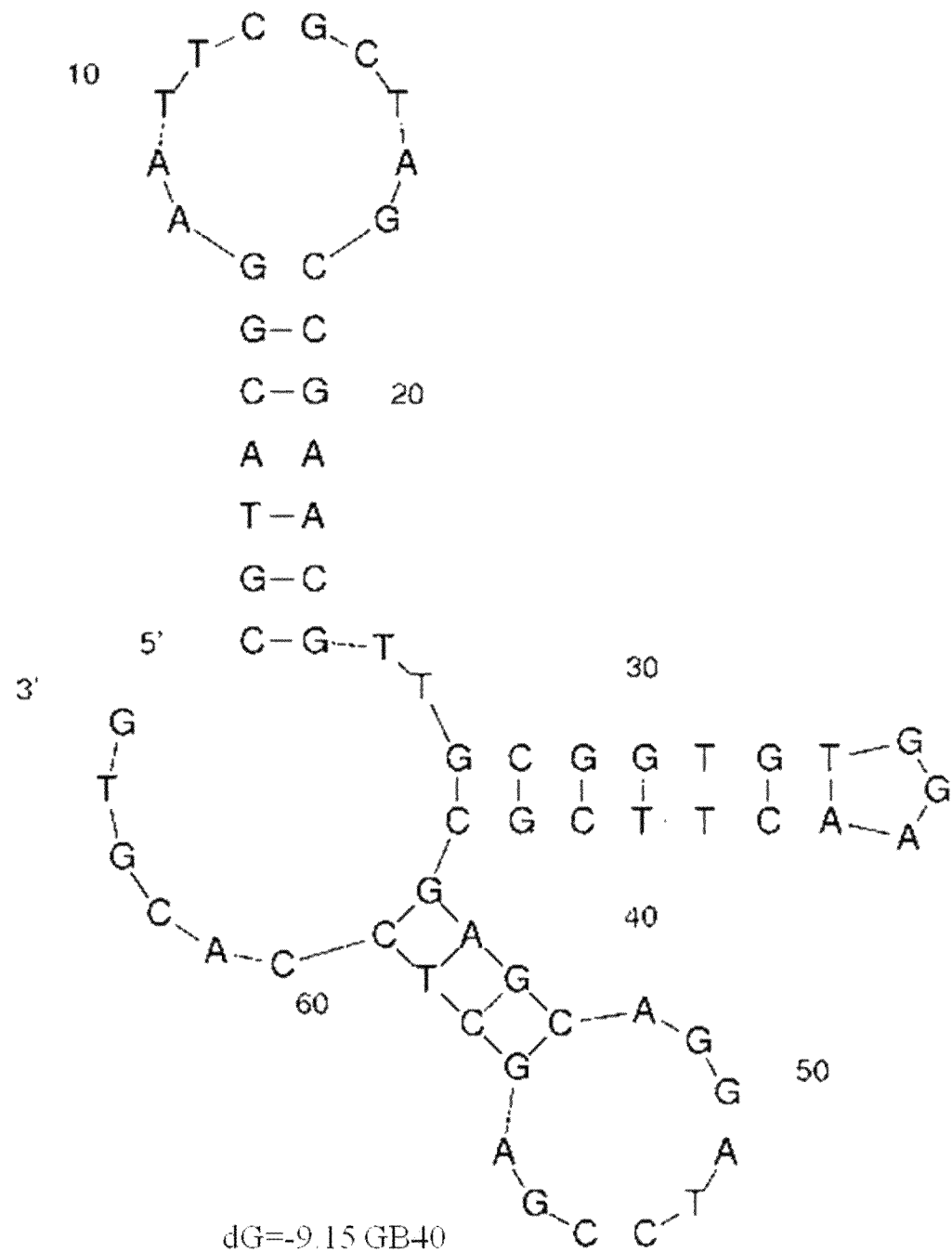
Figure 30:
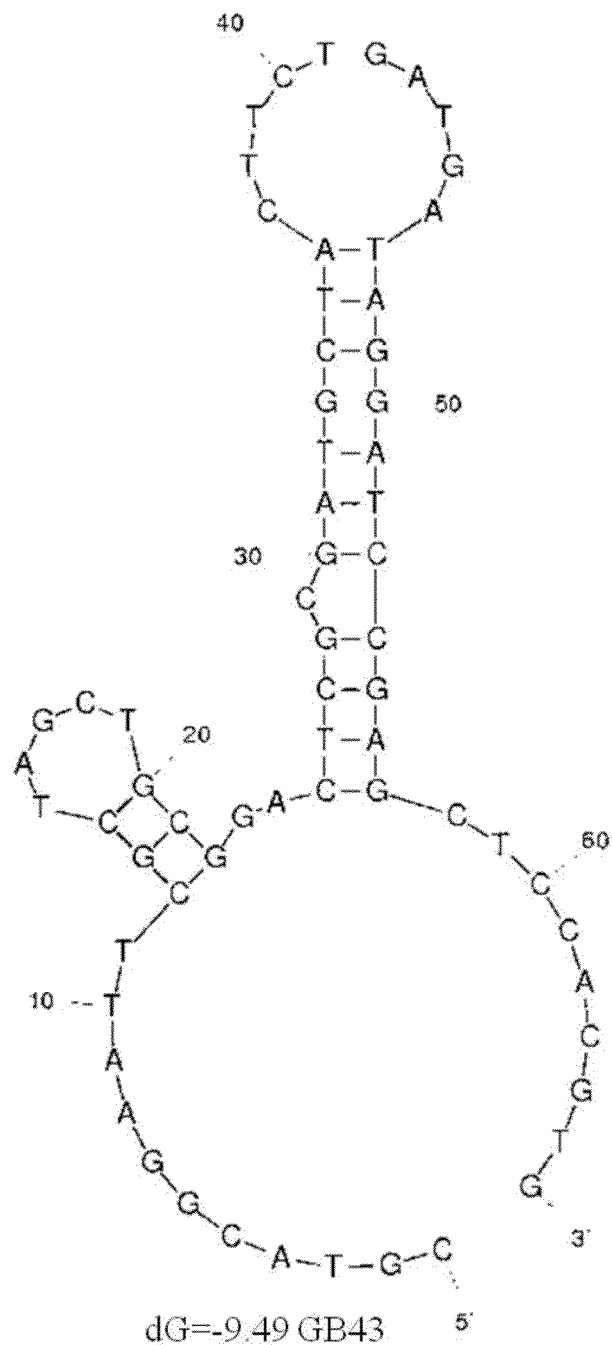

FIG. 20 illustrates a percentage of single-stranded DNA bound to a BVDV type 1 as a target material in each selection round.

The DNA pool finally obtained was cloned using a pDrive Cloning Vector (Qiagen, Netherlands), and DNA was extracted from a resultant colony to carry out a base sequence analysis. As a result, 10 kinds of DNAs specially bound to the BVDV type 1 were obtained. Base sequences of the DNAs were analyzed, and a result thereof is shown in Table 2.

Further, a result of prediction about secondary structures of these 10 kinds of aptamers using the M-fold program is shown in FIGS. 21 to 30.

TABLE 2

| SEQ ID NOS | Aptamer No. | Sequence (5'-3') |
|---|---|---|
| 19 | B1-13 | CGTACGGAATTCGCTAGCTTGGGTATAACGTTCTGAGTCAGAACGCCGGGATCCGAGCTCCACGTG |
| 20 | B1-38 | CGTACGGAATTCGCTAGCACGGCGGGTCGCCCGACTTTGGGCCGACTGGGATCCGAGCTCCACGTG |
| 21 | B1-34 | CGTACGGAATTCGCTAGCCGCTCGGGGCGCTGCACGTAGGGTGGGGTGGGATCCGAGCTCCACGTG |
| 22 | B1-17 | CGTACGGAATTCGCTAGCGTGGGGCAGTTGCTTGATGATCTGTAGCGCGGATCCGAGCTCCACGTG |
| 23 | B1-11 | CGTACGGAATTCGCTAGCTGCGCATCCACAAATGTATTGTCGGGGATGGATCCGAGCTCCACGTG |
| 24 | B1-39 | CGTACGGAATTCGCTAGCCGGGTCTAGTCAGGAGGTTCCTGTGGTGCTGGATCCGAGCTCCACGTG |

TABLE 2 -continued

| SEQ ID NOS | Aptamer No. | Sequence (5'-3') |
|---|---|---|
| 25 | B1-8 | CGTACGGAATTCGCTAGCGAGGGCGCCAAACAGGGT GTCCTGGCGTTGGGATCCGAGCTCCACGTG |
| 26 | B1-43 | CGTACGGAATTCGCTAGCTGCGGACTCGCGATGCTAC TTCTGATGATAGGATCCGAGCTCCACGTG |
| 27 | B1-27 | CGTACGGAATTCGCTAGCTAAGGGTAGCACAGGTCAC CTCGCCACTGTGGATCCGAGCTCCACGTG |
| 28 | B1-40 | CGTACGGAATTCGCTAGCCGAACGTTGCGGTGTGGAA CTTCGCGAGCAGGATCCGAGCTCCACGTG |

Example 5

Analysis on Bovine Viral Diarrhea Virus Binding Specificity

In order to confirm that aptamers specific to the 10 kinds of Bovine Viral Diarrhea Virus type 1 (BVDV type 1) separated in Example 4 did not show specificity to other similar substances, i.e., BVDV type 2 that is the most suitable control of the BVDV type 1, Classical Swine Fever Virus belonging to the same family, MDBK cells used to culture BVDV type 1, and Bovine Serum Albumin, but acted specifically to the BVDV type 1, the following experiment was carried out.

In order to carry out an SPR (Surface Plasmon Resonance) analysis, —COOH was formed on a surface of a gold chip with 50 mM 3,3'-dithiodipropionic acid, and then a self-assembly monolayer was formed with EDC/NHS. Then, streptavidin was immobilized thereon, and each aptamer of Example 4 bound to biotin was immobilized. Herein, the BVDV type 1 in the same amount and the similar substances (BVDV type 2, Classical Swine Fever Virus, MDBBK cells, and Bovine Serum Albumin) were reacted for 30 minutes in buffer solutions (100 mM NaCl, 2 mM $MgCl_2$, 5 mM KCl, 1 mM $CaCl_2$, and 20 mM Tris-Cl buffer solution containing 0.02% Tween 20, pH 7.6), respectively, and non-bound substances were washed off with the same buffer solutions.

Thereafter, a result of the SPR was analyzed with an Autolab springle (single channel, Eco Chemie, Netherlands) and it could be confirmed that all the 10 kinds of the aptamers showed high specificity to the BVDV type 1, and affinity of 3 kinds of aptamers observed to have the highest specificity to the BVDV type 1, i.e. an aptamer B1-11 (SEQ ID NO: 23), an aptamer B1-34 (SEQ ID NO: 21), and an aptamer B1-43 (SEQ ID NO: 26), is shown in FIG. 31.

As shown in FIG. 31, all of the aptamer B1-11 (SEQ ID NO: 23), the aptamer B1-34 (SEQ ID NO: 21), and the aptamer B1-43 (SEQ ID NO: 26) exhibited very high binding force with respect to the BVDV type 1 (BVDV t1) but did not bind well to the similar substances (CSFV, MDBK, and BSA) including BVDV type 2 (BVDV t2).

Such a result means that the nucleic acid aptamer specific to the BVDV type 1 of the present invention can specifically detect the BVDV type 1 and also makes it possible to diagnose bovine viral diarrhea more accurately.

Example 6

Measurement of Dissociation Constant ($K_d$) of Bovine Viral Diarrhea Virus Type 1

Aptamers B1-11, B1-34, and B1-43 had the highest specificity among the 10 kinds of aptamers specifically bound to the BVDV type 1 and produced in Example 4. Binding of these aptamers with respect to the BVDV type 1 was analyzed.

The aptamers were immobilized in the same manner as Example 3, and the BVDV type 1 at various concentrations was reacted for 30 minutes in buffer solutions (100 mM NaCl, 2 mM $MgCl_2$, 5 mM KCl, 1 mM $CaCl_2$, and 20 mM Tris-Cl buffer solution containing 0.02% Tween 20, pH 7.6). In order to obtain a dissociation constant, each reaction level was plotted by a nonlinear regression method and a single site saturation ligand binding method with Graphpad Prism 5.0. In this case, the equation $Y=B_{max}*X^h/(K_d\hat{A}h+X^h)$ was used (y represents a saturation degree, $B_{max}$ represents a maximal binding site, $K_d$ represents a dissociation constant, X represents non-bound Nampt, and h represents a hill slope constant).

As a result, the $K_d$ values of the three aptamers were obtained, and analysis data thereof is shown in FIG. 32.

FIG. 32 shows that all of the three aptamers exhibited high affinity with respect to the BVDV type 1.

Example 7

Detection of Bovine Viral Diarrhea Virus by Sandwich Binding Method

In order to find an optimum composition, i.e., a first aptamer (aptamer immobilized on a solid phase) and a second aptamer (aptamer bound to a target material bound to the first aptamer and labeled with a label), to detect a Bovine Viral Diarrhea Virus type 1 by a sandwich binding method (FIG. 33), the following experiment was carried out.

Firstly, with the three aptamers confirmed as having the highest affinity in Examples 5 and 6, one of the three aptamers (the aptamer B1-11 (SEQ ID NO: 23), the aptamer B1-34 (SEQ ID NO: 21), and the aptamer B1-43 (SEQ ID NO: 26)) was immobilized onto a gold chip in the same manner as Example 5 and bound to the BVDV type 1 and then additionally bound to any one of the three aptamers. Sequences of 9 combinations in total were tested, and results thereof were compared.

Figures 33, 34:
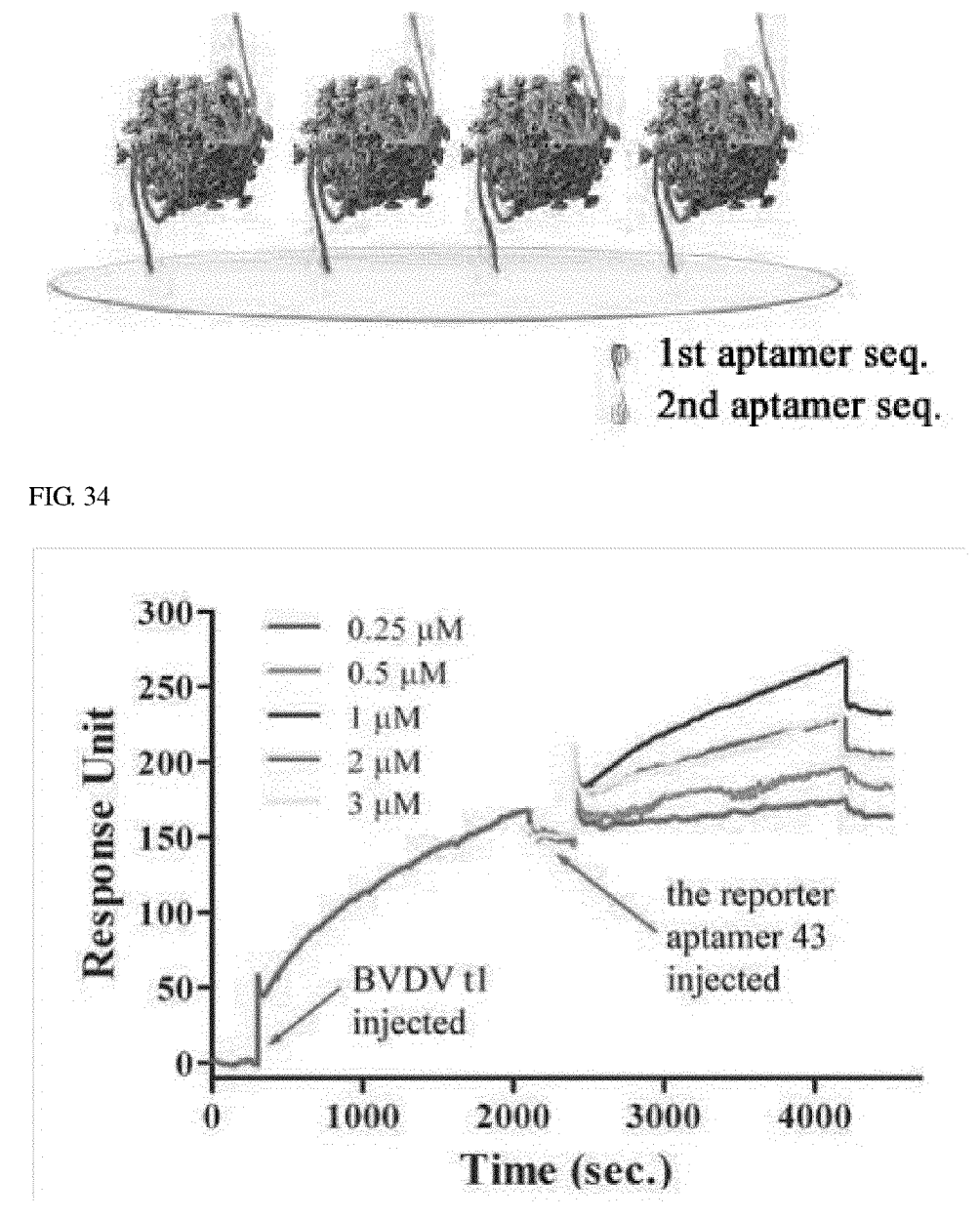

As a result, when the aptamer B1-11 (SEQ ID NO: 23) having the lowest $K_d$ was immobilized and the aptamer B1-43 (SEQ ID NO: 26) having the highest $K_d$ was reacted in a second-order reaction, the best result could be obtained as shown in FIG. 34. That is, in the case of a sandwich binding in which the aptamer B1-11 with SEQ ID NO: 23 was immobilized as a first aptamer on a solid phase, and the BVDV type 1 as a target material was added thereto and reacted with the aptamer B1-43 with SEQ ID NO: 26 as a second aptamer in a second-order reaction, the BVDV type 1 could be detected most sensitively.

The specific parts of the present invention have been described in detail. It is obvious to one of ordinary skill in the art that such detailed descriptions are merely provided to illustrate preferable embodiments and do not limit the scope of the present invention.

Therefore, the effective scope of the present invention shall be defined by the accompanying claims and their equivalents.

The present invention provides a technique capable of developing an aptamer using graphene without immobilizing a main target. Since the target is not immobilized, a binding site of the target is not limited, and thus it is possible to develop an aptamer having a high binding force with respect to the target. Further, since expensive and complicated equipment and skilled manpower are not needed, it is possible to readily develop an aptamer.

Furthermore, a Nampt protein used as a target model can be effectively detected using an aptamer, and thus it is possible to measure a concentration of the Nampt protein in blood more stably and sensitively as compared with an antibody-based analysis which has been conventionally used. Moreover, a DNA aptamer requires less production costs than an antibody and is easily immobilized on a surface, and thus it is useful in manufacturing a biosensor chip. With a biosensor capable of sensitively and accurately measuring a concentration of a Nampt protein in blood using a DNA aptamer specifically bound to Nampt, it is possible to more accurately diagnose Nampt related diseases such as type 2 diabetes, colorectal cancer, prostate cancer, breast cancer, stomach cancer, polycystic ovarian syndrome, chronic renal failure, chronic obstructive lung disease, etc.

Also, since a biosensor capable of diagnosing bovine viral diarrhea is developed using an aptamer specifically bound to a Bovine Viral Diarrhea Virus type 1 used as a target model, a more accurate diagnosis can be expected.

In addition, a sandwich detection technique using two or more kinds of the aptamer to detect a Bovine Viral Diarrhea Virus type 1 is capable of more sensitively detecting the virus through signal enhancement, and thus it is possible to accurately diagnose bovine viral diarrhea.

The present invention can be used as a kit for detecting or diagnosing proteins, low molecular materials, viruses, or diseases related thereto.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. A method for producing a nucleic acid aptamer without target immobilization comprising:
   reacting a single-stranded nucleic acid pool including a PCR primer region at both ends and any 30 to 50 bases at its center with a target material or a counter-target material and adding graphene; and
   separating a target specific nucleic acid aptamer by removing a target non-specific single-stranded nucleic acid bound to the graphene, or
   separating a target specific nucleic acid aptamer from the graphene by causing a conformational change by the target material on a target specific single-stranded nucleic acid bound to the graphene.

2. The method for producing a nucleic acid aptamer without target immobilization of claim 1, wherein the single-stranded nucleic acid is DNA or RNA.

3. The method for producing a nucleic acid aptamer without target immobilization of claim 1, further comprising:
   performing a graphene-based selection process and a counter selection process repeatedly one or more times using the target material and the counter-target material with respect to a single-stranded nucleic acid specifically bound to the target material.

4. The method for producing a nucleic acid aptamer without target immobilization of claim 3, wherein the graphene-based counter selection process includes separating a target specific aptamer from graphene by removing a target non-specific single-stranded nucleic acid bound to the counter-target material and causing a conformational change by the target material on a target specific single-stranded nucleic acid bound to the graphene.

5. The method for producing a nucleic acid aptamer without target immobilization of claim 1, wherein the target material includes a protein, a low molecular material having a molecular weight of 10 to 2000 daltons, or a virus.

6. The method for producing a nucleic acid aptamer without target immobilization of claim 5, wherein the protein includes a Nampt (Nicotinamide phosphoribosyltransferase) protein.

7. The method for producing a nucleic acid aptamer without target immobilization of claim 5, wherein the virus includes a Bovine Viral Diarrhea Virus type 1.

8. The method for producing a nucleic acid aptamer without target immobilization of claim 4, wherein the counter-target material includes adiponectin, RBP4 (Retinol Binding Protein 4), resistin, vaspin, or HSA (Human Serum Albumin).

9. The method for producing a nucleic acid aptamer without target immobilization of claim 4, wherein the counter-target material includes Bovine Viral Diarrhea Virus type 2 (BVDV type 2), CSFV (Classical Swine Fever Virus), MDBK (Mardin-Darby Bovine Kidney cell), or BSA (Bovine Serum Albumin).

10. The method for producing a nucleic acid aptamer without target immobilization of claim 1, wherein the target-specific nucleic acid aptamer has a sequence selected from the group consisting of the base sequences set forth in SEQ ID NOS: 4 to 28.

11. A nucleic acid aptamer having a sequence selected from the group consisting of the base sequences set forth in SEQ ID NOS: 4 to 18, wherein the nucleic acid aptamer is specifically bound to a Nampt protein.

12. A kit for detecting a Nampt protein comprising:
   a nucleic acid aptamer having a sequence selected from the group consisting of the base sequences set forth in SEQ ID NOS: 4 to 18, wherein the nucleic acid aptamer is capable of specifically binding to a Nampt protein.

13. A kit for diagnosing a Nampt related disease comprising:
   a nucleic acid aptamer having a sequence selected from the group consisting of the base sequences set forth in SEQ ID NOS: 4 to 18, wherein the nucleic acid aptamer is capable of specifically binding to a Nampt protein.

14. The kit for diagnosing a Nampt related disease of claim 13, wherein the Nampt related disease includes type 2 diabetes, colorectal cancer, prostate cancer, breast cancer, stomach cancer, polycystic ovarian syndrome, chronic renal failure, or chronic obstructive lung disease.

15. A composition for separating a Nampt protein comprising:
   a nucleic acid aptamer having a sequence selected from the group consisting of the base sequences set forth in SEQ ID NOS: 4 to 18, wherein the nucleic acid aptamer is capable of specifically binding to a Nampt protein.

* * * * *